United States Patent [19]

Gouka et al.

[11] Patent Number: 5,705,358
[45] Date of Patent: Jan. 6, 1998

[54] PROCESS FOR PRODUCING/SECRETING A PROTEIN BY A TRANSFORMED MOULD USING EXPRESSION/SECRETION REGULATING REGIONS DERIVED FROM A ASPERGILLUS ENDOXYLANASE II GENE

[75] Inventors: Robertus Johannes Gouka, The Hague; Cornelis Antonius van den Hondel, Gouda; Wouter Musters, Maassluis; Hein Stam, Diemen; Johannes Maria Verbakel, Maasland, all of Netherlands

[73] Assignee: Unilever Patent Holdings B.V., Vlaardingen, Netherlands

[21] Appl. No.: 244,686

[22] PCT Filed: Dec. 9, 1992

[86] PCT No.: PCT/EP92/02896

§ 371 Date: Jun. 7, 1994

§ 102(e) Date: Jun. 7, 1994

[87] PCT Pub. No.: WO93/12237

PCT Pub. Date: Jun. 24, 1993

[30] Foreign Application Priority Data

Dec. 9, 1991 [NL] Netherlands ............................ 9102051

[51] Int. Cl.[6] ............................ C12N 15/62; C12P 21/02
[52] U.S. Cl. ............................ 435/69.1; 435/172.3
[58] Field of Search ............................ 435/69.1, 68.1, 435/9.4, 172.3

[56] References Cited

FOREIGN PATENT DOCUMENTS

| 2024448 | 3/1991 | Canada . |
|---|---|---|
| 357127 | 3/1990 | European Pat. Off. . |
| 421919 | 4/1991 | European Pat. Off. . |
| 436858 | 7/1991 | European Pat. Off. . |
| 439997 | 8/1991 | European Pat. Off. . |
| 463706 | 1/1992 | European Pat. Off. . |
| 91/1978 | 12/1991 | WIPO . |

OTHER PUBLICATIONS

Ward, et al.: "Improved Production of Chymosin in Aspergillus by Expression as a Glucoamylase–chymosin Fusion", Bio/Technology, vol. 8, No. 5, May 1990, pp. 435–440.

WO,A,9 119 782—Dec. 26, 1991—see p. 7, line 32—p. 8, lien 7; figue 1—see p. 10, line 34, p. 11, line 12.

N. Roberts, R.P. Oliver, P.J. Punt and C.A.M.J.J. van den Hondel, Curr Genet, Expression of the *Escherichia coli* β–glucuronidase gene in Industrial and Phytopathogenic Filamentous Fungi Curr Genet (1989), 15:177–180.

Fuller, Enzymers Required for Yeast Prohormone Processing, Ann. Rev. Physiol., 1988, 50:345–62.

Gunnar von Heijne, A New Method for Predicting Signal Sequence Cleavage Site, Nucleic Acids Research, 1986, vol. 14, No. 11, pp. 4683–4690.

Sanger et al., DNA Sequencing with Chain–terminating Inhibitors, Proc. natl. Acad. Sci. USA, Dec. 1977, vol. 74, No. 12, pp. 5463–5467.

*Primary Examiner*—Robert A. Wax
*Assistant Examiner*—Gabriele E. Bugaisky
*Attorney, Agent, or Firm*—Cushman Darby & Cushman IP Group Pillsbury Madison & Sutro LLP

[57] ABSTRACT

Methods are described for the isolation and characterization of DNA sequences from *Aspergillus niger* var. awamori which are involved in the expression and secretion of endoxylanase II (exlA) by said Aspergillus mould. A process using these expression and/or secretion regulating regions to direct the production and optionally the secretion of proteins other than endoxylanase II by transformed moulds is provided.

13 Claims, 10 Drawing Sheets

Fig. 1A

```
          10                    30                    50
AGcCCTTTTA TCCgTCTgcc gTCcATTTAG CCAAATGTAG TCCATTTAGC CAAGTGCGGT
          70                    90                   110
CCATTTAGCC AAGACCAGTG GCTAGATTGG TGGCTACACA GCAAACGCAT GACTGAGACA
         130                   150                   170
CAACTATAGG ACTGTCTCTG GAAATAGGCT CGAGGTTGTT CAAGCGTTTA AGGTGATGCG
         190                   210                   230
GCAAAATGCA TATGACTAAG CTGCTTcATC TTGCAGGGGG AAGGGATAAA TAGTCTTTTT
         250        .          270                   290
CGCAGAATAT AAATAGAGGT AGAGTGGGCT CGCAGCAATA TTGACCAGCA CAGTGCTTCT
         310                   330                   350
CTTCCAGTTG CATAAATCCA TTCACCAGCA TTTAGCTTTC TTCAATCATC ATG AAG GTC
                                                        M   K   V
```

```
                     380                        400
ACT GCG GCT TTT GCA GGT CTT TTG GTC ACG GCA TTC GCC GCT CCT GTG CCG
 T   A   A   F   A   G   L   L   V   T   A   F   A   A   P   V   P
                420                     440                        460
GAA CCT GTT CTG GTG TCC CGA AGT GCT GGT ATT AAC TAC GTG CAA AAC TAC
 E   P   V   L   V   S   R   S   A   G   I   N   Y   V   Q   N   Y
                                |> mature xylanase
                  480                        500
AAC GGC AAC CTT GGT GAT TTC ACC TAT GAC GAG AGT GCC GGA ACA TTT TCC
 N   G   N   L   G   D   F   T   Y   D   E   S   A   G   T   F   S
              520                     540                     560
ATG TAC TGG GAA GAT GGA GTG AGC TCC GAC TTT GTC GTT GGT CTG GGC TGG
 M   Y   W   E   D   G   V   S   S   D   F   V   V   G   L   G   W
                        580                     600              620
ACC ACT GGT TCT TCT AA GTGAGTGACT GTATTCTTTA ACCAAAGTCT AGGATCTAAC
 T   T   G   S   S   N
```

```
GTTTTCTAG C GCT ATC ACC TAC TCT GCC GAA TAC AGT GCT TCT GGC TCC TCT
            A   I   T   Y   S   A   E   Y   S   A   S   G   S   S
              680                     700                     720
TCC TAC CTC GCT GTG TAC GGC TGG GTC AAC TAT CCT CAG GCT GAA TAC TAC
 S   Y   L   A   V   Y   G   W   V   N   Y   P   Q   A   E   Y   Y
                    740                     760
ATC GTC GAG GAT TAC GGT GAT TAC AAC CCT TGC AGC TCG GCC ACA AGC CTT
 I   V   E   D   Y   G   D   Y   N   P   C   S   S   A   T   S   L
              780                     800                     820
GGT ACC GTG TAC TCT GAT GGA AGC ACC TAC CAA GTC TGC ACC GAC ACT CGA
 G   T   V   Y   S   D   G   S   T   Y   Q   V   C   T   D   T   R
                    840                     860
ACT AAC GAA CCG TCC ATC ACG GGA ACA AGC ACG TTC ACG CAG TAC TTC TCC
 T   N   E   P   S   I   T   G   T   S   T   F   T   Q   Y   F   S
              880                     900                     920
GTT CGA GAG AGC ACG CGC ACA TCT GGA ACG GTG ACT GTT GCC AAC CAT TTC
 V   R   E   S   T   R   T   S   G   T   V   T   V   A   N   H   F
```

Fig. 1B

```
                940                         960
AAC TTC TGG GCG CAG CAT GGG TTC GGA AAT AGC GAC TTC AAT TAT CAG GTC
 N   F   W   A   Q   H   G   F   G   N   S   D   F   N   Y   Q   V
980                     1000                        1020
ATG GCA GTG GAA GCA TGG AGC GGT GCT GGC AGC GCC AGT GTC ACG ATC TCC
 M   A   V   E   A   W   S   G   A   G   S   A   S   V   T   I   S
              1050                        1070                1090
TCT TAA GGGAT AAGTGCCTTG GTAGTCGGAA GATGTCAACG GGAACTTTG TTCTCAGCTG
 S   *
             1110              1130              1150
GTGTGATGAT CGGATCCGGC CTCTGGTGGT TACATTGAGG CTGTATAAGT TATTCTGGGG
             1170              1190              1210
CCGAGCTGTC AGCGGCTGCG TTTCCAATTT GCACAGATAA TCAACTTTCg TTTTCTATCT
             1230              1250              1270
CTTGCGTTTC CACGCTGTTT ATCCTATCCA TAGATAATAT tTTgCCCAAT ACATATTATC
             1290              1310              1330
TATATACAAC TTGTTCGGTC GCAGTAGTCA CTCCGAGCAA GGCATTGGGA AATTGGGAGA
             1350              1370              1390
TGCGGGGTGC TGCGTACGCT CTAAGGTAGG GCATTTAAAG GGATATTTAG CCTCCAGATA
             1410              1430              1450
TTCTATACTA ACAGACTTCT AATGACTGCG GATAATATAG AGGGCAAGAA TTTCTACAGT
             1470              1490              1510
TCGACGCAGT TCAACGCAAT CAGAGAGGGA ATACTGATGA GAGTGCAATC AGTTAGAGAA
             1530              1550              1570
GGACAACATG GCAGTCTTAG TGTGAACTTA CATAACGATA TGGACTCTAG AAAAAAGGAA
             1590              1610              1630
GGAGCTCCGT CTATATATAG CGCCATTACG TGTATCTGAT GCTTGCCCAT TGCCACTGGG
             1650              1670              1690
TAGGGTGACT TTTTGAAGCG ACTCGACATA TAATATGACA AACTCATGCC CCCTTTGCAG
             1710              1730              1750
GAAACTTAGC TTTTCCTGCC TTGCTTTGAA GCCACAATTA TCACGAAACT CATTTAGAGA
             1770              1790              1810
TTTATCTTCC TGTAACGGAA ACAAATATTT CGGGATTGGA ATAGCCTTTT GCCGAACTCA
             1830              1850              1870
TTATTTTTTT GCGACGGTAA ATCTGGGAGT ATACGATGTC CTTTCACGTT TCTCAACAAA
             1890              1910              1930
ACTCTGCCGC ACCGGGTAAC CTACGGATAG TACTGTATCC AGACTCAGTT TTTCTAATAA
             1950              1970              1990
CAGGACACTG TGCAATTTGC GGGAAAATTC CTATGTATAT TACTTTCTCG TTGCATCTCA
             2010              2030              2050
AATATTGTGG CTTTTTGAGA CCCACACTAT GTCTTGCACA TATTGTACCA TCCTTGCTTG
    2059
AGGCCAATT
```

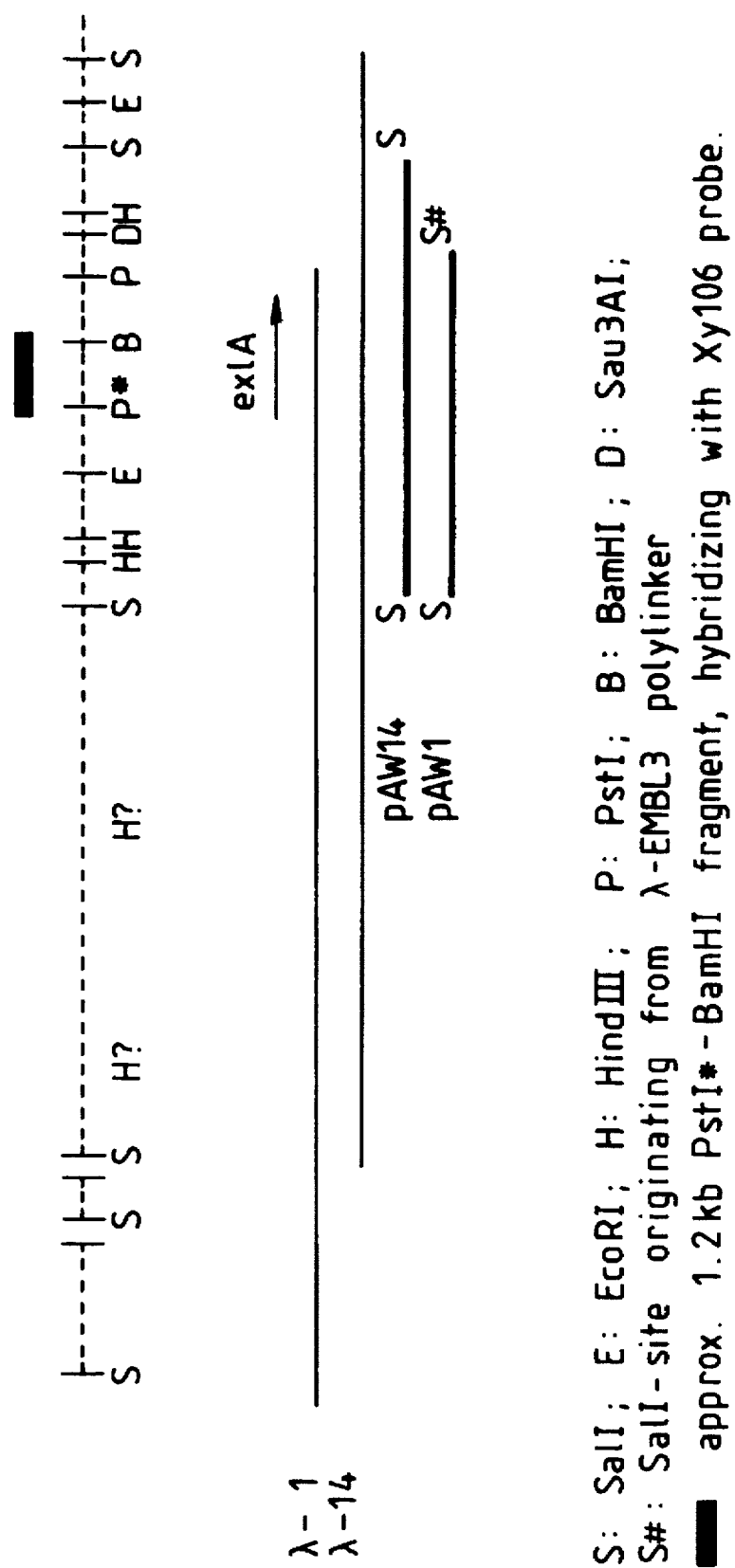

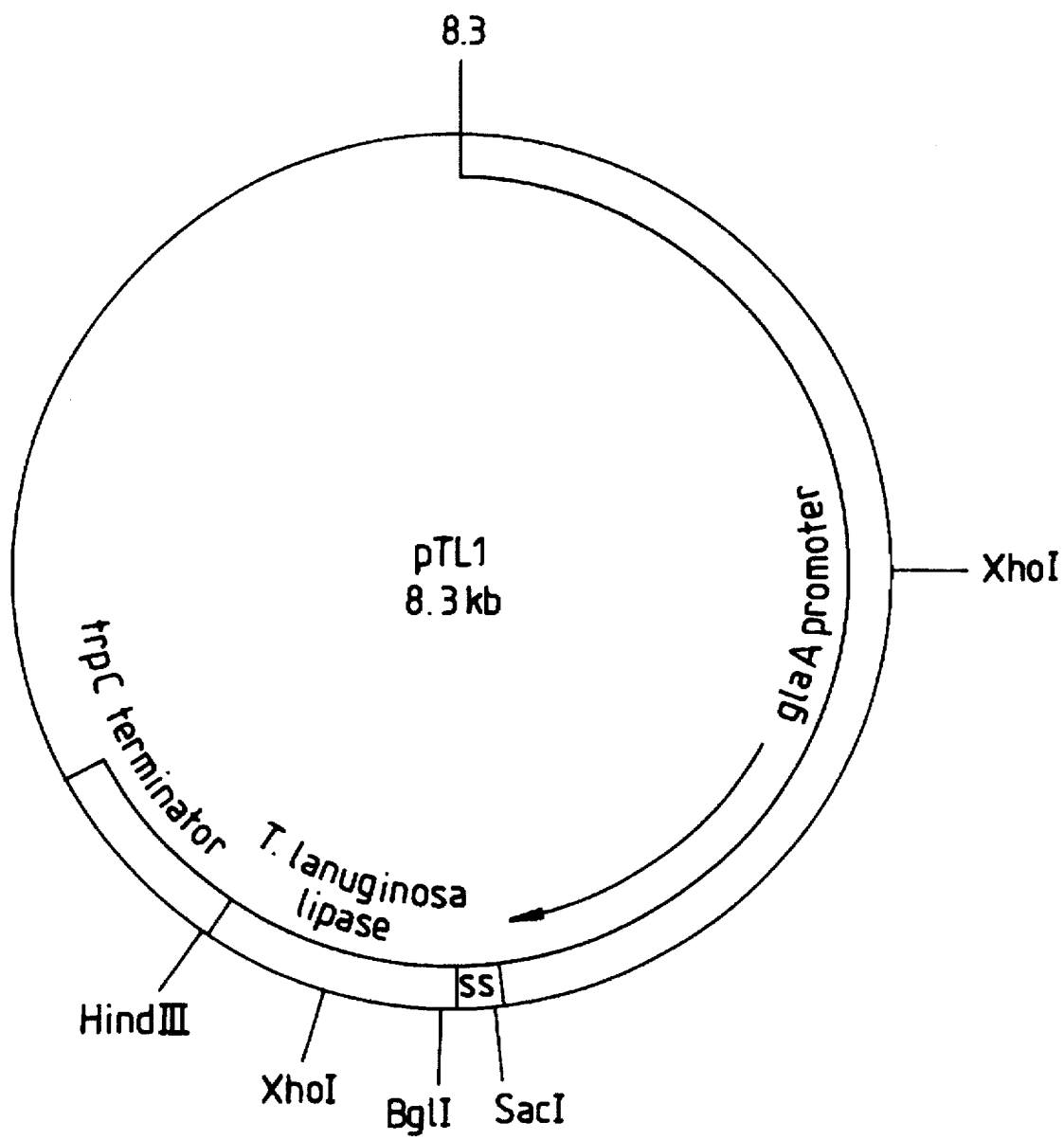

Fig.9.

```
  1  ATG AGG AGC TCC CTT GTG CTG TTC TTT GTC TCT GCG TGG ACG GCC TTG
      M   R   S   S   L   V   L   F   F   V   S   A   W   T   A   L

49  GCC AGT CCT ATT CGT CGA GAG GTC TCG CAA GAT CTG TTT AAC CAG TTC
      A   S   P   I   R   R   E   V   S   Q   D   L   F   N   Q   F
                              |> mature lipase 97  AAT CTC TTT GCA CAG TAT TCT GCT GCC GCA TAC TGC GGA AAA AAC AAT
      N   L   F   A   Q   Y   S   A   A   A   Y   C   G   K   N   N 145  GAT GCC CCA GCT GGT ACA AAC ATT ACG TGC ACG GGA AAT GCC TGC CCC
      D   A   P   A   G   T   N   I   T   C   T   G   N   A   C   P 193  GAG GTA GAG AAG GCG GAT GCA ACG TTT CTC TAC TCG TTT GAA GAC TCT
      E   V   E   K   A   D   A   T   F   L   Y   S   F   E   D   S 241  GGA GTG GGC GAT GTC ACC GGC TTC CTT GCT CTA GAC AAC ACG AAC AAA
      G   V   G   D   V   T   G   F   L   A   L   D   N   T   N   K 289  TTG ATC GTC CTC TCT TTC CGT GGC TCT CGT TCC ATA GAA AAC TGG ATC
      L   I   V   L   S   F   R   G   S   R   S   I   E   N   W   I 337  GGA AAT CTT AAC TTC GAC TTG AAA GAA ATA AAT GAC ATT TGC TCC GGC
      G   N   L   N   F   D   L   K   E   I   N   D   I   C   S   G 385  TGC AGG GGA CAT GAC GGC TTC ACC TCG AGC TGG AGG TCT GTA GCC GAT
      C   R   G   H   D   G   F   T   S   S   W   R   S   V   A   D 433  ACG TTA AGG CAG AAG GTG GAG GAT GCT GTG AGG GAG CAT CCC GAC TAT
      T   L   R   Q   K   V   E   D   A   V   R   E   H   P   D   Y 431  CGC GTG GTG TTT ACC GGA CAT AGC TTG GGT GGT GCA TTC GCA ACT GTT
      R   V   V   F   T   G   H   S   L   G   G   A   L   A   T   V 529  GCC GGA GCA GAC CTG CGT GGA AAT GGG TAT GAC ATC GAC GTG TTT TCA
      A   G   A   D   L   R   G   N   G   Y   D   I   D   V   F   S 577  TAT GGC GCC CCC CGA GTC GGA AAC AGG GCT TTT GCA GAA TTC CTG ACC
      Y   G   A   P   R   V   G   N   R   A   F   A   E   F   L   T 625  GTA CAG ACC GGC GGT ACC CTC TAC CGC ATT ACC CAC ACC AAT GAT ATT
      V   Q   T   G   G   T   L   Y   R   I   T   H   T   N   D   I 673  GTC CCT AGA CTC CCG CCG CGC GAG TTC GGT TAC AGC CAT TCT AGC CCA
      V   P   R   L   P   P   R   E   F   G   Y   S   H   S   S   P 721  GAG TAC TGG ATC AAA TCT GGA ACC CTT GTC CCC GTC ACC CGA AAC GAC
      E   Y   W   I   K   S   G   T   L   V   P   V   T   R   N   D 769  ATC GTG AAG ATA GAA GGC ATC GAT GCC ACC GGC GGC AAT AAC CAG CCT
      I   V   K   I   E   G   I   D   A   T   G   G   N   N   Q   P 817  AAC ATT CCG GAT ATC CCT GCG CAC CTA TGG TAC TTC GGG TTA ATT GGG
      N   I   P   D   I   P   A   H   L   W   Y   F   G   L   I   G

865  ACA TGT CTT TAG TGCGAAGCTT 886
      T   C   L
```

PROCESS FOR PRODUCING/SECRETING A PROTEIN BY A TRANSFORMED MOULD USING EXPRESSION/SECRETION REGULATING REGIONS DERIVED FROM A ASPERGILLUS ENDOXYLANASE II GENE

BACKGROUND OF THE INVENTION

The invention relates to a process for the production and optionally secretion of a protein by means of a transformed mould, into which an expression vector has been introduced with the aid of recombinant DNA techniques known per se, said vector comprising one or more mould-derived expression and/or secretion regulating regions controlling the expression of a gene encoding said protein and optionally controlling the secretion of the protein so produced. Such a process is known from various publications, in which the production of proteins with the aid of transformed moulds is described. Thus, in the non-prior-published patent application PCT/EP 91/01135 (UNILEVER, in the priority year published on 26 Dec. 1991 as WO 91/19782) there is described, inter alia, the production of a homologous endoxylanase II protein by a transformed Aspergillus strain.

Other ways of producing proteins by transformed moulds, in particular while using promoters originating from Aspergillus moulds, are known.

Ward, M. et al. (GENENCOR, 1990) have described the production by a transformed *Aspergillus niger* var. awamori of the milk-clotting enzyme chymosin or its precursor prochymosin. It was concluded that production of a fusion protein in which the prochymosin was connected with its N-terminus to the C-terminus of the Aspergillus protein glucoamylase gave a much higher secretion than with production of the prochymosin alone, whereby in both cases the protein was preceded by the glucoamylase signal sequence and under control of the glucoamylase promoter.

In CA-A-2024448 (ALLELIX BIOPHARMACE) "Recombinant DNA expression construct—containing promoter for use in Aspergillus", published on 1 Mar. 1991, the constitutive promoter of the *Aspergillus nidulans* aldehyde dehydrogenase gene and its use for the production of heterologous proteins in a transformed mould is described.

In EP-A-0436858 (GREEN CROSS CORP.) "Promoter of glyceraldehyde-3-phosphate dehydrogenase (GAPDH) gene—derived from *Aspergillus orizae*, used in new expression system in yellow-green or black koji mould", published on 17 Jul. 1991, the use of the promoter and terminator of the GAPDH gene in a vector for transforming a mould to produce foreign proteins is described.

and

In EP-A-0439997 (CIBA GEIGI AG) "*A. niger* pyruvate kinase promoter—used to construct vectors for expression of structural genes in suitable hosts", published on 7 Aug. 1991, the overproduction of a homologous gene product or a heterologous gene product in *A. niger* is described.

Moulds are organisms frequently used in the production of proteins and metabolites. A biotechnologically very important aspect of moulds is that they are capable of very efficient protein production and, if desired, secretion into the medium. It is also possible to grow moulds in a properly controlled way in large bioreactors. The combination of the possibilities of generating fungal biomass cost-effectively by means of fermentation and the high specific expression per cell make moulds exceptionally interesting hosts for the production of both heterologous and homologous proteins. For efficient production of these heterologous and homologous proteins, the use of an efficient promoter effective in moulds is essential. For secretion of a protein into the medium, specific sequences are required that cater for this. In connection with possible toxicity for the mould cell of the protein to be produced, it is also important that the activity of a promoter can be regulated, i.e. turned on at suitable moments, thus an inducible promoter is preferred.

SUMMARY OF THE INVENTION

The invention is based on the use of a non-prior-published promoter, which is described in more detail below, as well as on the use of other expression and/or secretion regulating regions, such as a terminator, a DNA sequence encoding a signal sequence, and a DNA sequence encoding at least an essential part of a mature endogenous mould protein.

In studies of the expression of proteins in moulds it was found that the enzyme endoxylanase type II (exlA) was efficiently produced after induction of expression of the exlA gene, and was also secreted efficiently into the medium. For production of that protein, the encoding gene was cloned together with its own promoter. In comparison with other mould promoters, the endoxylanase II promoter proved particularly efficient. Expression of the gene encoding the endoxylanase II enzyme (regulated by its own promoter) was found to be efficiently induced with various media components, including wheat bran, xylan and xylose. This induction was found to proceed efficiently in different mould strains (see WO 91/19782, UNILEVER). This provided an opportunity to obtain an efficient inducible promoter as well as other mould-derived expression and/or secretion regulating regions, including transcription terminator signals and secretion signals, which might perhaps be used for the production of heterologous and homologous proteins in moulds. The promoter fragment, terminator fragment and secretion signals of the *Aspergillus niger* var. awamori endoxylanase II gene were cloned and subsequently further defined. The *E. coli* β-glucuronidase gene (uidA) was used as an example of the production of a heterologous protein in a transformed mould. The promoter and terminator sequences of the *Aspergillus niger* var. awamori endoxylanase II gene were used for the construction of an expression vector. With the aid of this expression vector a heterologous gene encoding the *E. coli* protein β-glucuronidase was expressed in moulds under control of the endoxylanase II (exlA) promoter. By using exlA secretion signals, the heterologous and homologous proteins can also be secreted. As another example of the use of the exlA promoter and terminator for the production of heterologous proteins, a gene encoding a *Thermomyces lanuginosa* lipase was introduced in the expression vector under the control of exlA regulatory sequences, and used for the production and secretion of *Thermomyces lanuginosa* lipase. NOVO-NORDISK, an enzyme manufacturing company in Denmark, is marketing under the trade name "Lipolase" a lipase derived from *Thermomyces lanuginosa*, but produced by another microorganism. To illustrate that the exlA signal sequence can be used to direct the secretion of proteins other than exlA, a DNA sequence encoding a *Thermomyces lanuginosa* mature lipase amino acid sequence was fused to the exlA signal sequence and placed under the control of the exlA regulatory sequences in The above mentioned expression plasmid, and secretion of *Thermomyces lanuginosa* lipase was demonstrated.

Of course, the heterologous genes, of which the expression is exemplified in this specification, can be replaced by any DNA sequence encoding a desired protein (coding for enzymes, proteins, etc.) originating from a wide range of organisms (bacteria, yeasts, moulds, plants, animals and human beings) so that the desired protein can be produced by moulds.

Thus in one embodiment of the invention a process is provided for the production in transformed moulds of proteins other than endoxylanase type II using expression regulating sequences derived from the *Aspergillus niger* var. awamori endoxylanase II (exlA) gene, such as the promoter or the terminator, or functional derivatives of these regulatory sequences. In another embodiment of this invention, a process is provided by which proteins produced in moulds, if desired, can be secreted in the medium by making use of the DNA sequence encoding the signal sequence, in particular the pre-sequence or prepro-sequence, of the *Aspergillus niger* var. awamori endoxylanase II gene or functional derivatives of these sequences. Finally the invention also provides a process for producing a protein in which a vector is used comprising at least an essential part of the DNA sequence encoding the mature endoxylanase II protein, because it is known that in moulds an improved secretion of a heterologous protein can be obtained by initially producing it as a fusion protein comprising part of an endogenous mould protein (see also the Ward, M. et al. GENENCOR reference mentioned above).

BRIEF DESCRIPTION OF THE FIGURES AND TABLES

FIG. 1 shows the DNA sequence (SEQ ID NO:1) of the ca 2.1 kb PstI-PstI fragment of *Aspergillus niger* var. awamori present in the plasmid pAW14B, which fragment contains a gene coding for an endoxylanase II, indicated as the exlA gene. The translation start and the stop codon are doubly underlined. The 49 bp intron is underlined. The N-terminal end of the mature protein is indicated. The amino acid sequence (SEQ ID NO:2) of the protein (both of the pre(pro) form and of the mature protein) is indicated using the one-letter code.

FIG. 2 shows the restriction map of the genomic DNA region of *Aspergillus niger* var. awamori, comprising the exlA gene cloned in the phages lambda 1 and lambda 14. The used abbreviations stand for: S: SalI; E: EcoRI; H: HindIII; P: PstI; P*: PstI; B: BamHI; S#: SalI site originating from the polylinker of lambda-EMBL3; and D: Sau3A. The solid bar indicates a 1.2 kb PstI*-BamHI fragment hybridizing with Xyl06. P* and PstI* symbols are used to distinguish the two PstI sites present.

Figure 6:
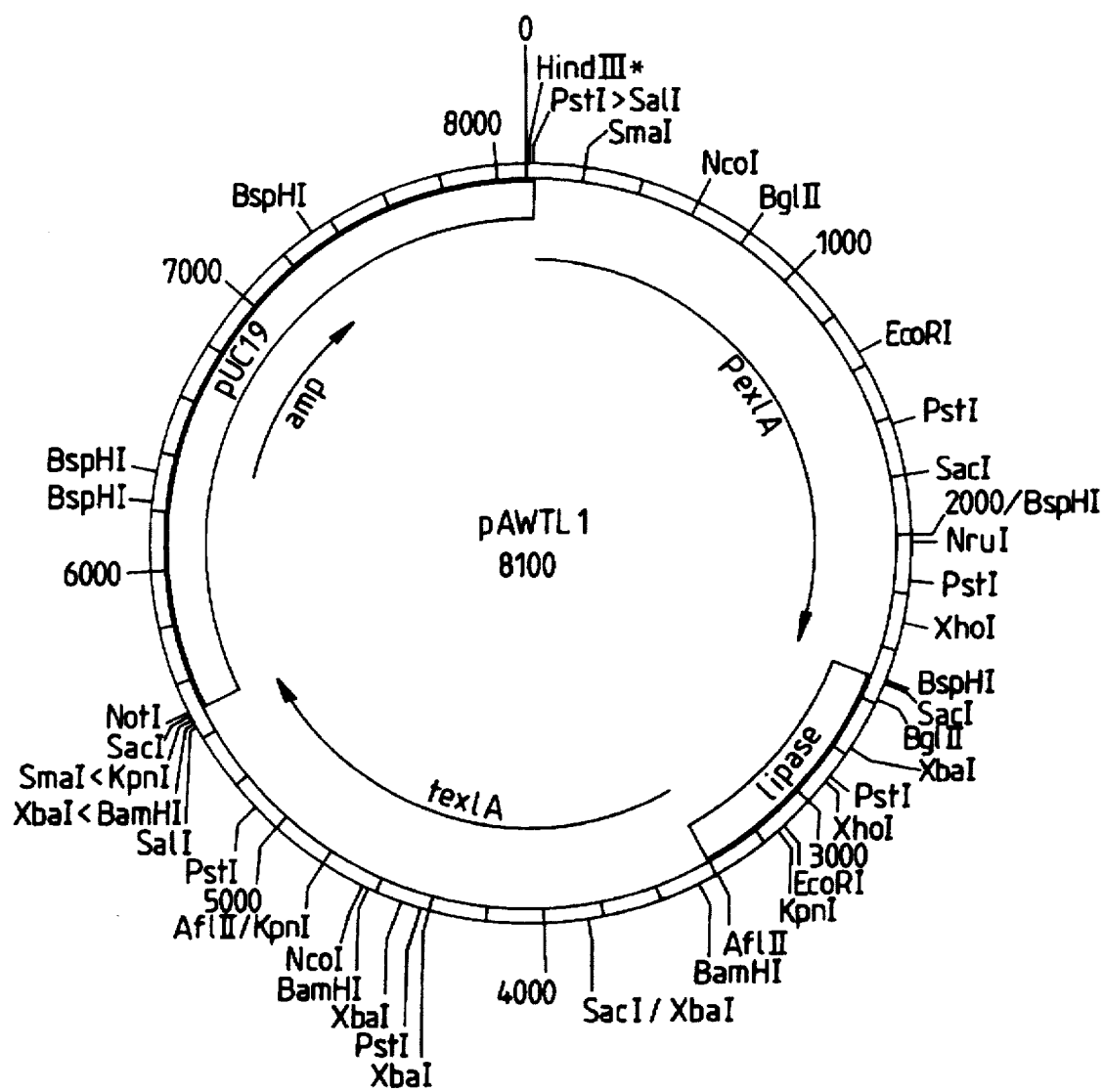

FIG. 6 shows plasmid pAWTL1 obtained by displacing the BspHI-AflII fragment comprising the exlA open reading frame in pAW14B with a BspHI-AflII fragment comprising a nucleotide sequence encoding the *T. lanuginosa* lipase together with its own pre-pro-sequence. Thus, plasmid pAWTL1 comprises the *T. lanuginosa* lipase gene together with its own pre-pro-sequence encoding region under the control of the *A. niger* var. awamori promoter and terminator.

Figure 7:
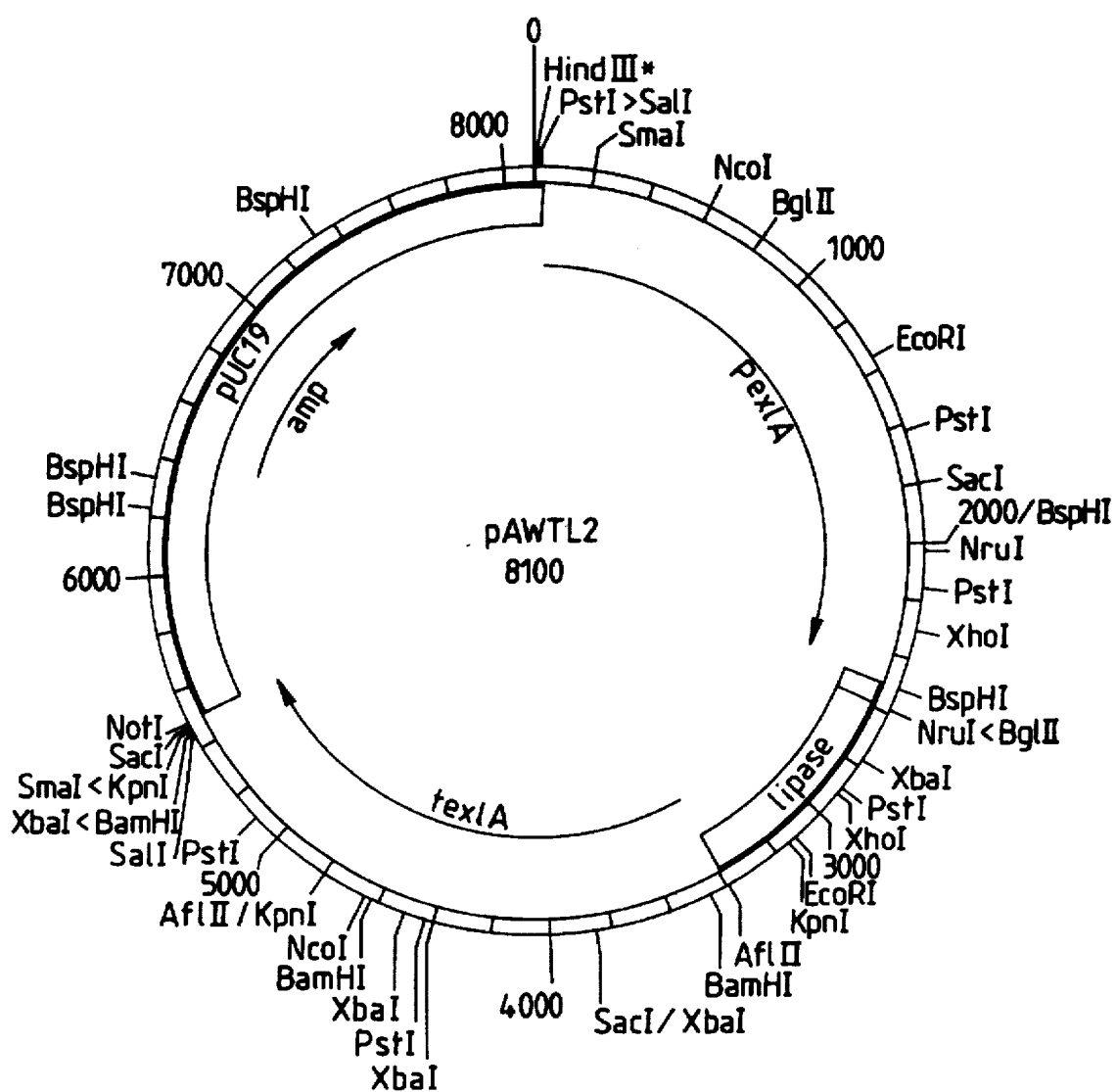

FIG. 7 shows plasmid pAWTL2 obtained by displacing the NruI-AflII fragment comprising the region encoding the mature exlA protein in pAW14B with a NruI-AflII fragment comprising a nucleotide sequence encoding the mature part of the *T. lanuginosa* lipase. Thus, plasmid pAWTL2 comprises the *T. lanuginosa* lipase gene fused to the exlA pre-pro-sequence encoding region under the control of the *A. niger* var. awamori promoter and terminator.

FIG. 8 shows plasmid pTL1 comprising a nucleotide sequence encoding the *T. lanuginosa* lipase together with its own pre-pro-sequence under the control of the *A. niger* gpdA promoter and the *A. nidulans* trpC terminator inserted in the polylinker of pUC18. The region encoding the pre-pro-sequence of the *T. lanuginosa* lipase is indicated by "ss"

FIG. 9 shows the sequence (SEQ ID.NO:3) comprising the open reading frame encoding the *T. lanuginosa* lipase as it is contained within plasmid pTL1. The N-terminal end (SEQ ID NO:4) of the mature protein is indicated.

Table A shows various probes derived from the N-terminal amino acid sequence of the endoxylanase II protein. These probes were used for the isolation of the exlA gene, see item 1.1 of Example 1.

The number of oligonucleotides present in the "mixed" probe is indicated in brackets; this number is obtained by including 1, 2, 3 or 4 different bases in every third position, depending on the number of codons for an amino acid. In Xyl04 nucleotides were selected on the basis of the hybridization G-C and G-T and/or on the basis of the preferred codons in *Aspergillus niger* glucoamylase. In Xyl05 and Xyl06 not all of the possibly occurring bases are introduced at the third position of the codons in order not to obtain more than 256 oligonucleotides in the mixture. The sequence of the oligonucleotides is complementary to that of the coding strand of the DNA, which resembles the corresponding mRNA.

Xyl01: a mixture of 256 oligos having a length of 23 deoxynucleotides the sequence of which is complementary to the part of the coding strand coding for the amino acids 5-12.

Xyl04: an oligo having a length of 47 deoxynucleotides the sequence of which is complementary to the part of the coding strand coding for the amino acids 2-17.

Xyl05: a mixture of 144 oligos having a length of 23 deoxynucleotides the sequence of which is complementary to the part of the coding strand coding for the amino acids 10-17.

Xyl06: a mixture of 256 oligos having a length of 47 deoxynucleotides the sequence of which is complementary to the part of the coding strand coding for the amino acids 2-17.

Table B shows various single-stranded subclones of lambda 1 and lambda 14 fragments, which were used for determination of the sequence of the exlA gene, see item 1.2 of Example 1.

Table C shows the results of *E. coil* β-glucuronidase production by non-transformed and transformed strains of the mould *Aspergillus niger* var. awamori, see item 2.2 of Example 2.

Table D shows that functional lipase was produced and secreted after induction of the exlA promoter by xylose, and that the secretion of a heterologous (*Thermomyces lanuginosa*) mature protein was directed in *Aspergillus niger* var. awamori by using either the exlA signal sequence (see AWLPL2-2) or the *Thermomyces lanuginosa* signal sequence (see AWLPL1-2), see item 3.2 of Example 3.

Table E shows various nucleotide sequences of oligonucleotides used in constructions described in Examples 1–3. see items 1.4, 2.1, 3.1.1, 3.1.2, 3.1.3, and 3.1.4. The sequence listing numbers refer to the listings provided in the official format.

DETAILED DESCRIPTION OF THE INVENTION

Since the endoxylanase II gene is expressed and the resulting protein is secreted very efficiently under appropriate cultivation conditions by *Aspergillus niger* var. awamori, the present invention is directed in particular to the cloning of the regulatory regions of the *Aspergillus niger* var. awamori endoxylanase II (exlA) gene, such as the promoter sequence, terminator sequence and signal sequence, and using these components for the development of a process for the production of proteins in moulds. The invention therefore relates generally to a process making use of a nucleic acid sequence derivable from a mould and comprising at least a regulatory region derivable from a gene encoding a polypeptide having endoxylanase II activity. Said nucleic acid sequence can be combined with nucleic acid sequences encoding other homologous or heterologous genes to bring these genes under the control of at least one exlA regulatory sequence.

"Nucleic acid sequence" as used herein refers to a polymeric form of nucleotides of any length, both to ribonucleic acid (RNA) sequences and deoxyribonucleic acid (DNA) sequences. In principle this term refers to the primary structure of the molecule. Thus this term includes both single and double stranded DNA, as well as single stranded RNA and modifications thereof.

In general the term "protein" refers to a molecular chain of amino acids with a biological activity and does not refer to a specific length of the product and if required can be modified in vivo or in vitro. This modification can for example take the form of amidation, carboxylation, glycosylation, or phosphorylation; thus inter alia peptides, oligopeptides and polypeptides are included. In this specification both terms, polypeptide and protein, are used as synonyms unless a specific meaning is clear from the context.

The invention also relates to the use of a vector containing the nucleic acid sequences as described for the production of proteins other than *Aspergillus niger* var. awamori endoxylanase II (exlA) and also relates to the use of microorganisms containing said vectors or nucleic acid sequences for producing said proteins.

The invention is also directed at the use of modified sequences of the aforementioned nucleic acid sequences according to the invention for the production of proteins other than *Aspergillus niger* var. awamori endoxylanase II (exlA), said modified sequences also having regulatory activity. The term "a modified sequence" covers nucleic acid sequences having the regulatory activity equivalent to or better than the nucleic acid sequence derivable from a mould and comprising at least a regulatory region derivable from a gene encoding a protein having endoxylanase II activity. Such an equivalent nucleic acid sequence can have undergone substitution, deletion or insertion or a combination of the aforementioned of one or more nucleotides resulting in a modified nucleic acid sequence without concomitant loss of regulatory activity occurring. Processes for the production of proteins other than *Aspergillus niger* var. awamori endoxylanase II (exlA) using such modified nucleic acid sequences fall within the scope of the present invention. In particular processes for the production of proteins other than *Aspergillus niger* var. awamori endoxylanase II (exlA) using modified sequences capable of hybridizing with the non-modified nucleic acid sequence and still maintaining at least the regulatory activity of the non-modified nucleic sequence fall within the scope of the invention.

The expression "functional derivatives" used in the claims refers to such modified sequences.

The term "a part of" covers a nucleic acid sequence being a subsequence of the nucleic acid sequence derivable from a mould and comprising at least a regulatory region derivable from a gene encoding a polypeptide having endoxylanase II activity. In particular the invention is directed at a process using a nucleic acid sequence derivable from a mould of the genus Aspergillus. A suitable example of a mould from which a nucleic acid sequence according to the invention can be derived is an Aspergillus of the species *Aspergillus niger*, in particular *Aspergillus niger* var. awamori. In particular the strain *Aspergillus niger* var. awamori CBS 115.52 (ATCC 11358) is eminently suitable for deriving a nucleic acid sequence according to the invention. Preferably the nucleic acid sequence for use in a process according to the invention comprises at least a promoter as regulatory region. The nucleic acid sequence for use in a process according to the invention can also comprise an inducer or enhancer sequence enabling a higher level of expression of any nucleic acid sequence operably linked to the promoter. It is also possible for the nucleic acid sequence for use in a process according to the invention to comprise a termination signal as regulatory region. The nucleic acid sequence for use in a process according to the invention can comprise one or more regulatory regions. A nucleic acid sequence for use in a process according to the invention can comprise solely the promoter as regulatory region or a combination thereof with an enhancer or other functional elements. A nucleic acid sequence for use in a process according to the invention can also further comprise terminator sequences, although these are not always required for efficient expression of the desired expression product.

According to a further embodiment of the invention a nucleic acid sequence for use in a process according to the invention can further comprise a sequence encoding a secretory signal necessary, for secreting a gene product from a mould. This will be preferred when intracellular production of a desired expression product is not sufficient and extracellular production of the desired expression product is required.

Secretory signals comprise the prepro- or pre-sequence of the endoxylanase II gene for example. A secretory signal derivable from the endoxylanase II gene of an Aspergillus mould is particularly favoured. The specific embodiment of the nucleic acid sequence used in a process according to the invention will however depend on the goal that is to be achieved upon using a process according to the invention. "Signal sequence" as used herein generally refers to a sequence of amino acids which is responsible for initiating export of a protein or polypeptide chain. A signal sequence, once having initiated export of a growing protein or polypeptide chain, can be cleaved from the mature protein at a specific site. The term also includes leader sequences or leader peptides. The preferred signal sequence herein is the deduced signal sequence from the *Aspergillus niger* var. awamori endoxylanase II gene given in FIG. 1.

With the help of DNA oligonucleotides deduced from protein sequence analysis of endoxylanase II from *Aspergillus niger* var. awamori chromosomal DNA fragments comprising the entire endoxylanase II (exlA) gene of *Aspergillus niger* var. awamori including the regulatory regions, such as the promoter, the signal sequence and the termination sequence have been isolated from a genomic library. The regulatory regions of the endoxylanase II (exlA) gene have been used for the production and, if desired, secretion of proteins other than endoxylanase II, e.g. heterologous proteins, by *Aspergillus niger* var. awamori. The invention is therefore in particular directed at a process in which one or more of the regulatory regions of the *Aspergillus niger* var. awamori endoxylanase II gene or equivalent nucleic acid sequences are used for the production of proteins other than endoxylanase II in *Aspergillus niger* var. awamori. The term "equivalent nucleic acid sequence" has the same meaning as given above for "a modified nucleic acid sequence".

In the Examples given below the expression and secretion potential of the obtained exlA promoter and the exlA signal sequences have been tested by constructing new vectors for expression of a heterologous β-glucuronidase gene and the production and secretion of a heterologous lipase in Aspergillus. The resulting constructs were tested in *Aspergillus niger* var. awamori.

Thus in a general form the invention provides a process for the production and optionally secretion of a protein different from the endoxylanase type II protein ex *Aspergillus niger* var. awamori by means of a transformed mould, into which an expression vector has been introduced with the aid of recombinant DNA techniques known per se, said vector comprising mould-derived expression and/or secretion regulating regions, in which process at least one of said expression and/or secretion regulating regions is selected from (1) the expression and secretion regulating regions of the endoxylanase II gene (exlA gene) of *Aspergillus niger* var. awamori present on plasmid pAW14B (FIG. 3), which is present in a transformed *E. coli* strain JM109 deposited at the Centraalbureau voor Schimmelcultures in Baarn, The Netherlands, under N° CBS 237.90 on 31 May 1990, and (2) functional derivatives thereof also having expression and/or secretion regulating activity.

In a preferred embodiment of the invention the selected expression regulating region is a promoter and said vector comprises a gene encoding said protein under control of said promoter, the latter being selected from (1) the promoter of the endoxylanase II gene (exlA gene) of *Aspergillus niger* var. awamori present on plasmid pAW14B (FIG. 3), which is present in a transformed *E. coli* strain JM109 deposited at the Centraalbureau voor Schimmelcultures in Baarn, The Netherlands, under N° CBS 237.90 on 31 May 1990, and (2) functional derivatives thereof also having promoter activity. More preferably said promoter is equal to the promoter present on the 5' part upstream of the exlA gene having a size of about 2.5 kb located between the SalI restriction site at position 0 and the start codon ATG of the exlA gene in plasmid pAW14B. in particular said promoter comprises at least the polynucleotide sequence 1–350 according to FIG. 1.

This promoter can be induced by wheat bran, xylan, or xylose, or a mixture of any combination thereof, present in a medium in which the transformed mould is incubated, whereby the use of xylose as inducing agent is preferred.

In another preferred embodiment of the invention the selected expression regulating region is a terminator and said vector comprises a gene encoding said protein followed by said terminator, the latter being selected from (1) the terminator of the endoxylanase II gene (exlA gene) of *Aspergillus niger* var. awamori present on plasmid pAW14B (FIG. 3), which is present in a transformed *E. coli* strain JM109 deposited at the Centraalbureau voor Schimmelcultures in Baarn, The Netherlands, under N° CBS 237.90 on 31 May 1990, and (2) functional derivatives thereof also having terminator activity. Preferably, said terminator is equal to the terminator present on the 3' part downstream of the exlA gene having a size of about 1.0 kb located right downstream of the stop codon (TAA) of the exlA gene in plasmid pAW14B.

A further embodiment of the invention is a process for the production and secretion of a protein different from the endoxylanase type II protein ex *Aspergillus niger* var. awamori by means of a transformed mould, in which process the selected secretion regulating region is a DNA sequence encoding a signal sequence and said vector comprises a gene encoding said protein preceded by said DNA sequence encoding a signal sequence, the latter being selected from (1) the DNA sequence encoding the signal sequence of the endoxylanase II gene (exlA gene) of *Aspergillus niger* var. awamori present on plasmid pAW14B (FIG. 3), which is present in a transformed *E. coli* strain JM109 deposited at the Centraalbureau voor Schimmelcultures in Baarn, The Netherlands, under N° CBS 237.90 on 31 May 1990, and (2) functional derivatives thereof also directing secretion of the protein. Preferably, the gene (1) encoding said protein is also preceded by at least an essential part of a DNA sequence (2) encoding the mature endoxylanase II protein, whereby said DNA sequence (2) is present between said DNA sequence encoding a signal sequence (3) and the gene (1). A preferred signal sequence is the signal sequence encoded by polynucleotide 351–431 of the DNA sequence given in FIG. 1, which polynucleotide precedes the DNA sequence in plasmid pAW14B encoding the mature exlA polypeptide. Summarizing, in a process for producing a protein according to the invention the vector used for transforming a mould can comprise an exlA -derived promoter as hereinbefore described or a exlA -derived terminator as hereinbefore described or a exlA -derived signal sequence as hereinbefore described or at least an essential part of the exlA structural gene, or any combination of these expression and/or secretion regulating regions.

The invention is illustrated with the following Examples without being limited thereto. All techniques used for the manipulation and analysis of nucleic acid materials were performed essentially as described in Sambrook et al. (1989), except where indicated otherwise.

EXAMPLE 1

Cloning and characterization of the endoxylanase II gene (exlA) and associated regulating sequences of *Aspergillus niger* var. awamori 1.1 Isolation of the *Aspergillus niger* var. awamori exlA gene In order to isolate the exlA gene from chromosomal DNA of *Aspergillus niger* var. awamori different probes were synthesized consisting of mixtures of oligonucleotides (Table A). The composition of these mixtures was derived from the N-terminal amino acid sequence of purified endoxylanase II protein.

By means of Southern blot analysis it was established that in digests of chromosomal DNA—under stringent conditions—only one band hybridizes with the probes used. In the EcoRI, SalI and BamHI digest of *Aspergillus niger* var. awamori DNA one band of respectively 4.4, 5.3 and 9.5 kb hybridizes with both Xyl01, Xyl04 and Xyl06. With Xyl05 no clear signal was found at 41° C. On the basis of this result a gene bank of *Aspergillus niger* var. awamori DNA was hybridized at 65° C. with the oligonucleotide mixture Xyl06 as a probe. Of the 65000 tested plaques (corresponding to 32 times the genome) three plaques (lambda 1, 14 and 63) hybridized with this probe. After hybridization of digests of lambda 1 and lambda 14 DNA with Xyl06 a hybridizing band of >10 kb was found in the EcoRI digest of lambda 1. The size of the hybridizing band in the lambda 14 and the chromosomal EcoRI digest was 4.4. kb. In the SalI digest of lambda 1 a 4.6 kb band hybridizes; in the SalI digest of lambda 14 this is, like in chromosomal DNA, a 5.3 kb band. Also a 1.2 kb PstI-BamHI fragment (FIG. 2) hybridizes with Xyl06. On the basis of restriction patterns with different enzymes and cross-hybridization of lambda 1 and lambda 14 digests with the 5.3 kb SalI fragment of lambda 14 it was confirmed that these lambda's contained overlapping fragments of the genome of *Aspergillus niger* var. awamori. Also homologous hybridization of total induced RNA with respectively lambda 1, lambda 14 and the 5.3 kb SalI fragment of lambda 14 confirmed the presence of exlA sequences on these lambda's. Hybridization was found with a xylan-induced MRNA of ca. 1 kb. The size thereof corresponds to that of the mRNA molecule hybridizing with Xyl06.

1.2 Subcloning of the *Aspergillus niger* var. awamori exlA gene

Figure 3:
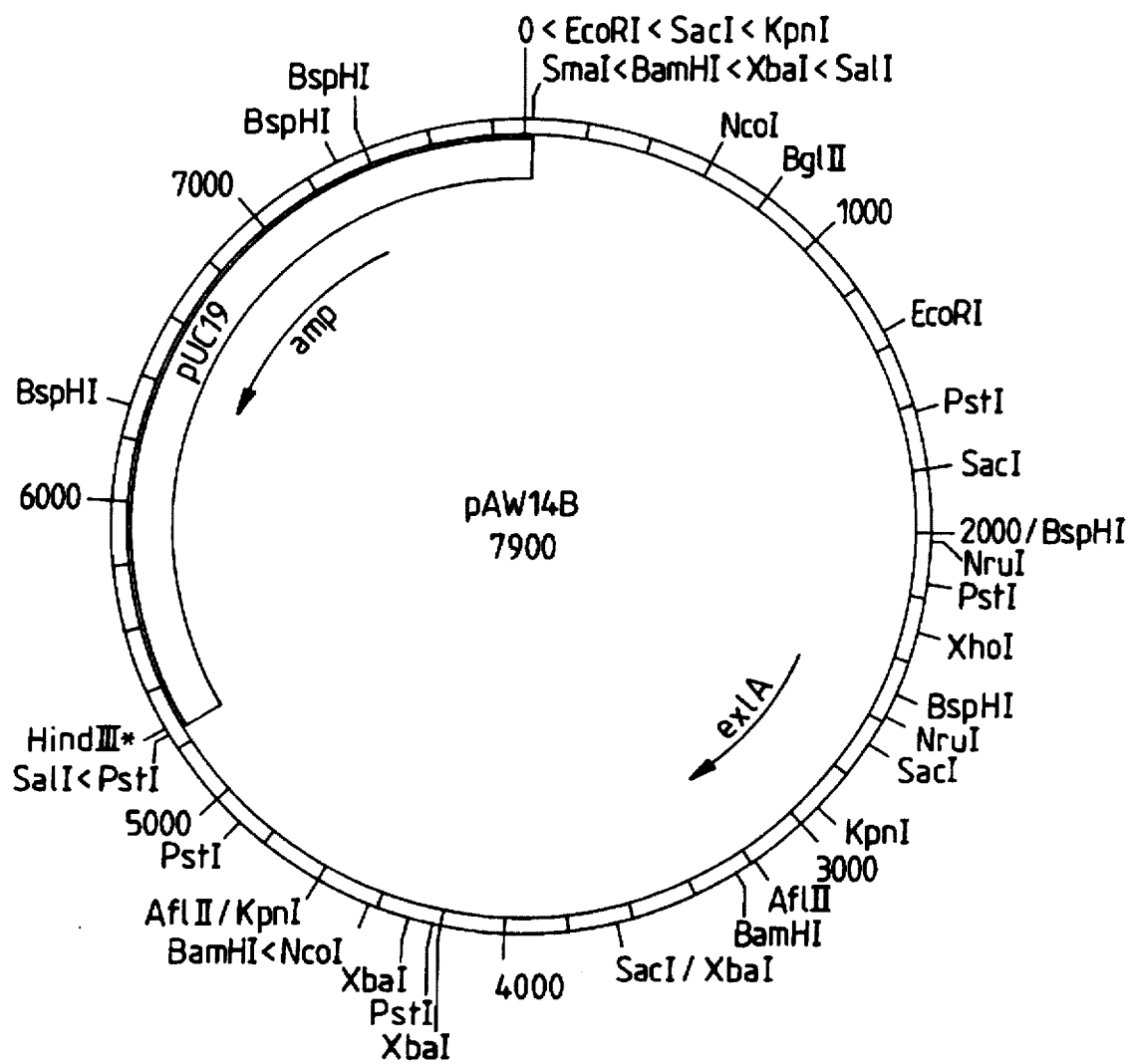
FIG. 3 shows the plasmid PAW14B obtained by insertion of the 5.3 kb SalI fragment comprising the exlA gene of *Aspergillus niger* var. awamori in the SalI site of pUC19.

The SalI fragments hybridizing with Xyl06 of respectively lambda 1 (4.6 kb) and lambda 14 (5.3 kb) were cloned in two orientations in the SalI site of pUC19, which resulted in respectively plasmid pAW1 (A and B) and plasmid pAW14 (A and B, see FIG. 3). The 1.2 kb PstI*-BamHI fragment hybridizing with Xyl06 and the adjacent 1.0 kb

TABLE A

Probes derived from the N-terminal amino acid sequence of the endoxylanase II protein Amino acid sequence
1           5              10             15
Ser Ala Gly Ile Asn Tyr Val Gln Asn Tyr Asn Gly Asn Leu Gly Asp Phe Probe   Bases   Amino acids   (number of oligonucleotides)

Base sequence 3'-5'

Xyl01   23   5–12            (256)
             TTA ATA CAX GTT TTA ATA TTA CC
              G   G     C     G   G   G

Xyl04   47   2–17            (1)
             CGG CCG TAG TTG ATG CAG GTC TTG ATG TTG CCG TTG GAC CCG CTG AA

Xyl05   23   10–17           (144)
                             ATG TTG CCA TTA AAX CCA CTG AA
                                          G    G G        G
                                                C         C

Xyl06   47   2–17            (256)
             CGG CCG TAG TTG ATG CAG GTC TTG ATG TTG CCG TTG GAG CCG CTG AA
              C   C   C         C   T                     C         C   C

X = A, G, C or T

The number of oligonucleotides present in the "mixed" probe is indicated in brackets; this number is obtained by including 1, 2, 3 or 4 different bases in every third position, depending on the number of codons for an amino acid. In Xyl04 a G was selected on the basis of the hybridization G-C and G-T and/or on the basis of the preferred codons in *Aspergillus niger* glucoamylase. In Xyl05 and Xyl06 not all possibly occurring bases have been introduced at the third position of the codons in order to obtain no more than 256 oligonucleotides in the mixture. The sequence of the oligonucleotides is complementary to that of the coding strand.

Xyl01: a mixture of 256 oligos having a length of 23 deoxynucleotides the sequence of which is complementary to the part of the coding strand coding for the amino acids 5–12.

Xyl04: an oligo having a length of 47 deoxynucleotides the sequence of which is complementary to the part of the coding strand coding for the amino acids 2–17.

Xyl05: a mixture of 144 oligos having a length of 23 deoxynucleotides the sequence of which is complementary to the part of the coding strand coding for the amino acids 10–17.

Xyl06: a mixture of 256 oligos having a length of 47 deoxynucleotides the sequence of which is complementary to the part of the coding strand coding for the amino acids 2–17.

BamHI-PstI fragment from respectively pAW14A and pAW1A were subcloned into M13mp18 and M13mp19 cut with BamHI and PstI, resulting in the m18/m19 AW vectors of Table B.

TABLE B

Single-stranded subclones of lambda 1 and lambda 14 fragments

| Fragment | Resulting vectors |
|---|---|
| pAW 1A BamHI-PstI* (1.2 kb) | m18AW 1A-1/m19AW 1A-1 |
| pAW14A BamHI-PstI* (1.2 kb) | m18AW14A-1/m19AW14A-1 |
| pAW 1A PstI-BamHI (1.0 kb) | m18AW 1A-2/m19AW 1A-2 |
| pAW14A PstI-BamHI (1.0 kb) | m18AW14A-2/m19AW14A-2 |

1.3 Determination of the transcription direction of the exlA gene

The transcription direction of the exlA gene was established by means of spot blot hybridization of ss-DNA of respectively m18AW14A-1 and m19AW14A-1 with Xyl06. It was found that ss-DNA of m19AW14A-1 (5'-PstI*-BamHI-3') hybridizes with this probe. Because the sequence of Xyl06 is equal to that of the non-coding strand, m19AW14A-1 contains the coding strand. On the basis thereof the transcription direction shown in FIG. 2 was determined. This direction is confirmed by the results of a primer extension experiment.

1.4 Identification of the exlA gene

The DNA sequence of a part of the promoter region was determined by sequence analysis of pAW14B with Xyl06 as a primer (5' part of the gene). In this region a primer Xyl11 (see Table E) was selected, with which the DNA sequence of complementary strand of m18AW14A-1 and m18AW1A-1 was determined. The results showed that these vectors contained a DNA sequence which was substantially equal to that of Xyl06, while the amino acid sequence derived from the base pair sequence was identical with the N-terminal amino acid sequence of the mature endoxylanase II protein. Thus the cloning of at least the 5' end of the exlA gene had been proven. The presence of the entire exlA gene in the vectors pAW14 and pAW1 seemed plausible on the basis of the position of the 5' end of the gene on the SalI fragments (FIG. 2) and the size of the exlA mRNA (ca. 1 kb).

1.5 Sequence analysis

The nucleotide sequence of the exlA gene and surrounding regions was established in two directions in both the m13AW14 and the m13AW1 subclones by means of the dideoxy procedure (Sanger et al., 1977). The sequence around the BamHI site located downstream of the PstI* site (FIG. 2) was established by sequence analysis of double-stranded pAW14 and pAW1 DNA. Compressions were cleared up by using dITP instead of dGTP. in the independent clones lambda 1 and lambda 14 an identical exlA sequence was established. The complete nucleotide sequence of the 2.1 kb PstI*-PstI fragment comprising the entire pre(pro) endoxylanase II gene and the promoter and terminator sequences of the endoxylanase II gene is shown in FIG. 1. The mature endoxylanase II protein is preceded by a leader peptide of 27 amino acids. A predicted recognition site for the signal peptidase is present between the alanine residues at the positions 16 and 17 (. .-T-A-F-A-↓-A-P-V-. .) (Van Heijne, 1986). From the length of the leader peptide it can be derived that in the protein a second processing site is present. Cleavage of the bond between Arg (27) and Ser (28) presumably is performed by a KEX2-like endoprotease (Fuller et al., 1988).

1.6 Localization of the intron

In the exlA gene the presence of an intron of either 49 or 76 bp (581–629 or 581–656, see FIG. 1 ) was predicted on the basis of the presence of sequences corresponding to "donor" and "acceptor" sites of introns in aspergilli. Definite proof of the absence of a 76 bp intron was obtained by isolation of an endoxylanase II derived peptide with the sequence Tyr-Ser-Ala-Ser-Gly . . . This peptide can only be localized in the protein starting from nucleotide position 652 (see FIG. 1). Therefore, the exlA gene comprises a single, 49 bp intron (position 581–629, see FIG. 1).

1.7 Determination of the 3' end of the exlA gene

The position of the stop codon of the exlA gene (position 1033–1035 in FIG. 1) was derived from DNA sequence data. This stop codon was confirmed, since the amino acid sequence of one of the peptides derived from endoxylanase II by chemical cleavage with CNBr proved to be identical to the C-terminal amino acid sequence derived from DNA sequence data (position 991–1032 in FIG. 1).

1.8 Evaluation of DNA and protein data

On the basis of the above data it was established that the gene coding for endoxylanase II of *Aspergillus niger* var. awamori had been cloned on a 5.3 kb SalI fragment. The DNA sequence of the gene, the position of the intron and the length of the mRNA were established. The established N-terminal amino acid sequence of the mature protein was fully confirmed by the DNA sequence. On the basis of the above data it can be concluded that the exlA gene codes for a protein of 211 amino acids and that the first 27 amino acids are removed post-translationally. From this data the exlA signal sequence was derived.

Also, the nucleotide sequence of the exlA promoter follows from the obtained sequence (see FIG. 1, position 1–350). Also, the nucleotide sequence of the exlA terminator follows from the obtained sequence (see FIG. 1, position 1036–2059 or a part thereof).

EXAMPLE 2

Expression of the *Escherichia coli* β-glucuronidase (uidA) gene using the exlA promoter and terminator sequences.

2.1 Construction of the uidA expression vector

The uidA expression plasmid (pAW15-1) was constructed starting from plasmid pAW14B, which contains a ca. 5.3 kb SalI fragment on which the 0.7 kb endoxylanase II (exlA) gene is located, together with 2.5 kb of 5'- flanking sequences and 2.0 kb of 3'-flanking sequences (FIG. 3). In pAW14B the exlA coding region was replaced by the uidA coding region. A BspHI site (5'-TCATGA-3') comprising the first codon (ATG) of the exlA gene and an AflII site (5'-CTTAAG-3'), comprising the stopcodon (TAA) of the exlA gene facilitated the construction of pAW15-1.

Figure 4:
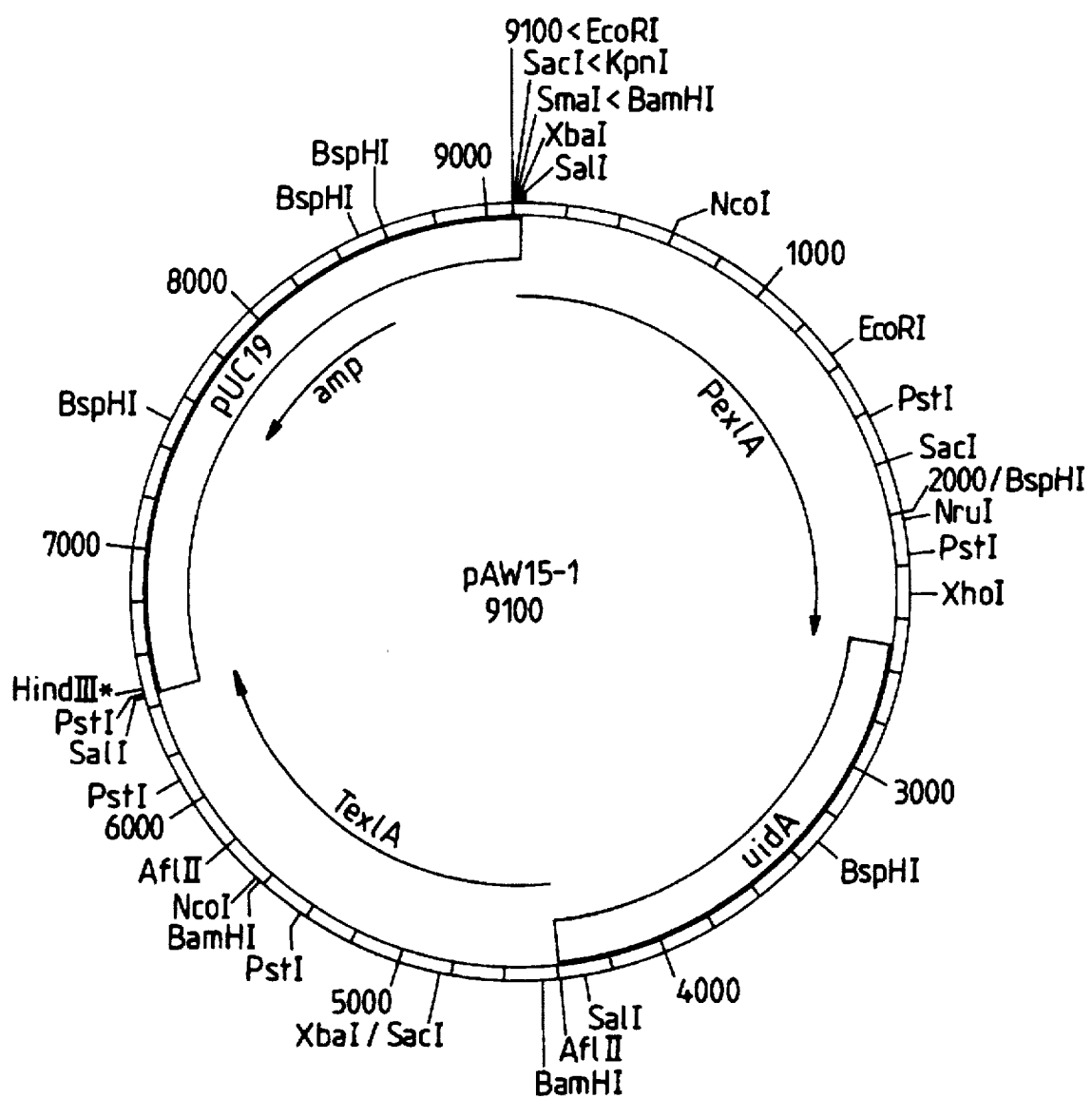
FIG. 4 shows the plasmid pAW15-1 obtained by displacing the BspHI-AflII fragment comprising the exlA open reading frame in pAW14B with a NcoI-AflII fragment comprising the *E. coli* uidA coding sequence. Thus, plasmid pAW15-1 comprises the *E. coli* uidA gene under the control of the *A. niger* var. awamori promoter and terminator.

The construction was carried out as follows: pAW14B (7.9 kb) was cut partially with BspHI (pAW14B contains five BspHI sites) and the linearized plasmid (7.9 kb) was isolated from an agarose gel. Subsequently the isolated 7.9 kb fragment was cut with BsmI, which cuts a few nucleotides downstream of the BspHI site of interest, to remove plasmids linearized at the other BspHI sites. The fragments were separated on an agarose gel and the 7.9 kb BspHI-BsmI fragment was isolated. This was partially cut with AflII and the resulting 7.2 kb BspHI-AflII fragment was isolated. The uidA gene was isolated as a 1.9 kb NcoI -AflII fragment from pNOM-AflII, a plasmid derived from pNOM102 (Roberts et al., 1989). In pNOM102 two NcoI sites are present, one of which is located at the 5'-end of the uidA gene and comprises the ATG-startcodon for translation of the gene. The second NcoI site is located a few nucleotides downstream of the stopcodon. To obtain an AflII site downstream of the uidA stopcodon the latter NcoI site was converted into an AflII site: pNOM102 was cut partially with NcoI and ligated with a NcoI-AflII linker (Nco-Afl, see Table E), resulting in vector pNOM-AflII. The 7.2 kb BspHI-AflII fragment of pAW14B was ligated to the 1.9 kb NcoI-AflII fragment of pNOM-AflII to give vector pAW15-1 (FIG. 4).

Figure 5:
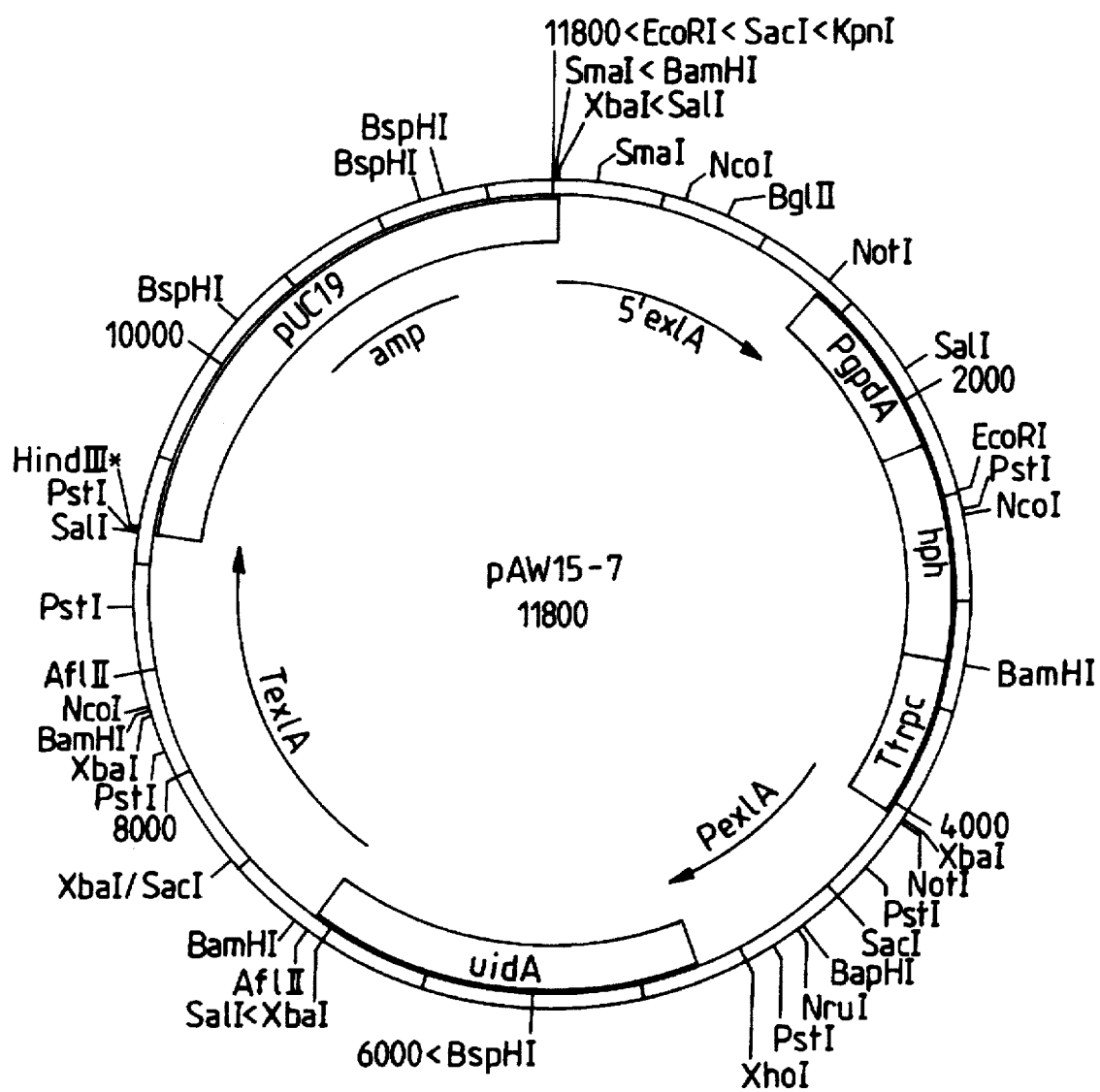
FIG. 5 shows plasmid pAW15-7 obtained by inserting a 2.6 kb NotI fragment comprising the *E. coli* hygromycin resistance gene controlled by the *A. nidulans* gpdA promoter and the *A. nidulans* trpC terminator in the EcoRI site of pAW15-1.

The constructed vector (pAW15-1) can subsequently be transferred to moulds (for example *Aspergillus niger*, *Aspergillus niger* var. awamori, *Aspergillus nidulans* etc.) by means of conventional co-transformation techniques and the β-glucuronidase can then be expressed via induction of the endoxylanase II promoter. The constructed vector can also be provided with conventional selection markers (e.g. amdS or pyrG, hygromycin etc.) and the mould can be transformed with the resulting vector to produce the desired protein. As an example, the *E. coli* hygromycin selection marker was introduced in the uidA expression vector, yielding pAW15-7 (FIG. 4). For this purpose a fragment containing the *E. coli* hygromycin resistance gene controlled by the *Aspergillus nidulans* gpdA promoter and the *Aspergillus nidulans* trpC terminator was used. This cassette was isolated as a 2.6 kb NotI fragment from pBluekan7-1 in which the hygromycin resistance cassette is flanked by NotI sites. In pAW15-1 a NotI site was created by converting the EcoRI site (present 1.2 kb upstream of the ATG codon) into a NotI site using a synthetic oligonucleotide (Eco-Not, see Table E), yielding pAW15-1-Not. The 2.6 kb NotI fragment from pAWBluekan7-1 was isolated and ligated with NotI-linearized pAW15-1-Not. The resulting vector was called pAW15-7 (FIG. 5).

2.2 Production of *E. coli* β-glucuronidase driven by exlA expression signals pAW15-7 was used to transform *Aspergillus niger* var. awamori. Transformant AW15.7-1 was identified by hygromycin selection and by Southern hybridization analysis of genomic DNA of this transformant it was established that this transformant contains a single copy of the uidA gene.

*Aspergillus niger* var. awamori (AW) and transformant AW15.7-1 were grown under the following conditions: shake flasks (500 ml) with 200 ml synthetic media (pH 6.5) were inoculated with spores (final concentration: 10E6/ml).

The medium had the following composition (AW Medium):

| sucrose | 10 g/l | NaNO$_3$ | 6.0 g/l |
|---|---|---|---|
| KCl | 0.52 g/l | KH$_2$PO$_4$ | 1.52 g/l |
| MgSO$_4$.7H$_2$O | 0.49 g/l | Yeast extract | 1.0 g/l |
| ZnSO$_4$.7H$_2$O | 22 mg/l | H$_3$BO$_3$ | 11 mg/l |
| MnSO$_4$.4H$_2$O | 5 mg/l | FeSO$_4$.7H$_2$O | 5 mg/l |
| CaCl$_2$.6H$_2$O | 1.7 mg/l | CuSO$_4$.5H$_2$O | 1.6 mg/l |
| NaH$_2$MoO$_4$.2H$_2$O | 1.5 mg/l | Na$_2$EDTA | 50 mg/l |

Incubation took place at 30° C., 200 rpm for 24 hours in a Mk X incubator shaker. After growth cells were removed by filtration (0.45 µm filter), washed twice with AW Medium without sucrose and yeast extract (salt solution), resuspended in 50 ml salt solution and transferred to 300 ml shake flasks containing 50 ml salt solution to which xylose has been added to a final concentration of 10 g/l (induction medium). The moment of resuspension is referred to as "t=0" (start of induction). Incubation took place under the same conditions as described above. Samples were taken 15 and 22 hours after induction. Biomass was recovered by filtration over miracloth, dried by squeezing and immediately frozen in liquid nitrogen. The mycelium was disrupted by grinding the frozen mycelium and β-glucuronidase activity was determined essentially as described in Roberts et al. (1989)

From Table C it is evident that the exlA promoter is specifically induced by the presence of xylose, and that the exlA promoter and terminator can be used for the production of *E. coli* β-glucuronidase in transformant AW15.7-1.

TABLE C

| | β-glucuronidase production | | | |
|---|---|---|---|---|
| Strain | exp. | t = 0 | t = 15 | t = 22 |
| AW | A | 0.0 | 0.0 | 0.1 |
| AW | B | 0.0 | 0.1 | 0.0 |
| AW15.7-1 | A | 0.7 | 1110 | 823 |
| AW15.7-1 | B | 0.6 | 1065 | 773 |

Transformants were grown on synthetic medium as indicated in the text for 24 hours and at t=0 were transferred to induction medium as indicated in the text. β-glucuronidase activity in the mycelium was determined as described in the text and is expressed in arbitrary units of enzymatic activity per milligram total protein.

EXAMPLE 3

Production and secretion of the *Thermomyces lanuginosa* lipase using the exlA promoter, signal sequence and terminator.

3.1 Construction of expression plasmids based on the exlA expression signals 3.1.1 Vector Plasmid pAW14A-Not was the starting vector for construction of a series of expression plasmids containing the exlA expression signals and the gene coding for *Thermomyces lanuginosa* lipase. Plasmid pAW14A comprises an *Aspergillus niger* var. awamori chromosomal 5 kb SalI fragment on which the 0.7 kb exlA gene is located, together with 2.5 kb of 5'-flanking sequences and 2.0 kb of 3'-flanking sequences (similar to pAW14B. see FIG. 3). In pAW14A the EcoRI site originating from the pUC19 polylinker was converted to a NotI site by insertion of a synthetic oligonucleotide (Eco-Not. see Table E), yielding pAW14A-Not.

Starting from pAW14A-Not, constructs were made in which the exlA promoter (2.5 kb) was fused to the translation-initiation codon (ATG) of the *Thermomyces lanuginosa* lipase gene. Also, constructs were made in which the exlA promoter and the DNA sequence coding for the first 27 amino acids of the exlA protein, which is the preprosequence, was fused to the sequences coding for the mature lipase polypeptide.

In both series of expression vectors the exlA transcription terminator was used.

The following vector fragments were isolated from pAW14A-Not and used for the constructions:

for the fusion with the translation-initiation codon of the lipase a 7.2 kb BspHI-AflIII fragment was isolated from pAW14A-Not. This is a similar fragment as the one isolated for the construction of pAW15-1 (see example 2) and was isolated essentially by the same approach as described in Example 2. The fragment contains 2.5 kb nucleotide sequences comprising the exlA promoter up to the BspHI site which comprises the ATG codon, and 2.0 kb nucleotide sequences comprising the exlA transcription terminator starting with the AflIII site which comprises the stopcodon.

for the fusion of the exlA promoter and exlA pre-propeptide encoding region (the first 27 amino acids of the exlA gene) with the coding region of the mature lipase polypeptide, a partially digested 7.2 kb NruI-AflIII fragment was isolated from pAW14A-Not. This fragment contains 2.5 kb nucleotide sequences comprising the exlA promoter and the coding sequence of the first 26 amino acids of the exlA protein (preprosequence), which ends with a NruI site, thus lacking only 1 amino acid of the exlA prosequence. Furthermore the fragment comprises 2 kb nucleotide sequences comprising the exlA transcription terminator starting with the AflII site.

The *Thermomyces lanuginosa* lipase gene was isolated from vector pTL-1, which comprises a 0.9 kb coding region of the lipase gene (FIG. 9) flanked by the *Aspergillus niger* glaA promoter and the *Aspergillus nidulans* trpC transcription terminator (FIG. 8).

3.1.2 Fusion of the lipase gene with the exlA transcription terminator sequence

To obtain a fusion of the exlA transcription terminator with the lipase gene, an AflII site was created just downstream of the stopcodon of the lipase gene. In pTL-1 a HindIII site is present 5 base pairs downstream of the stopcodon of the lipase gene (FIGS. 8 and 9), in which an AflII site was created using a synthetic oligonucleotide. The construction was carried out as follows:

pTL-1 was cut with HindIII, yielding a linear 8.3 kb fragment, which was isolated from an agarose gel and ligated with the oligonucleotide Hind-Afl (see Table E). In the resulting vector, pTL1-AflII the HindIII site has disappeared and an AflII site has been created just downstream of the stopcodon of the lipase gene, thus preparing the lipase gene for fusion to the exlA terminator at the AflII site.

3.1.3 Fusion of the exlA promoter with the lipase gene (ATG fusion)

pTL1-AflII was used as starting vector to isolate a DNA fragment comprising the lipase gene. To fuse the lipase gene to the exlA promoter the region of the lipase gene comprising the ATG codon (ATATGA) was converted to a BspHI site (TCATGA). This site still comprises the correct coding sequence of the lipase gene. For this purpose a synthetic DNA fragment was used, consisting of oligonucleotides BTFF09 and BTFF10 (see Table E) annealed to each other. This synthetic fragment contains a XhoI site for cloning, followed by a BspHI site comprising the ATG codon and the next 7 base pairs of the lipase gene up to the SacI site.

Vector pTLI-AflII was linearized by partial digestion with XhoI, followed by cutting with SacI which cuts after position +10 of the open reading frame encoding the lipase pre-pro-polypeptide. The 6.3 kb XhoI-SacI vector fragment (resulting from a cut at the XhoI site in the glaA promoter while leaving the internal XhoI site in the lipase gene intact, see FIG. 8) was isolated from an agarose gel and ligated with the synthetic XhoI-SacI fragment resulting in vector pTL1-XS. From pTL1-XS a 0.9 kb BspHI-AflII fragment comprising the lipase gene was isolated and ligated to the 7.2 kb BspHI-AflII fragment from pAW 14A-Not yielding expression vector pAWTL-1 (FIG. 6).

3.1.4 Fusion of the exlA promoter and the region encoding the exlA prepro sequence with the coding sequence of the lipase mature protein pTL1-AflII was used as starting vector to isolate a DNA fragment comprising the lipase gene. To obtain a correct fusion of the sequence encoding the lipase mature polypeptide with the exlA promoter sequence and the exlA leader peptide encoding sequences, a synthetic DNA fragment was used, consisting of oligonucleotides BTFF05 and BTFF06 (see Table E) annealed to each other. This synthetic fragment comprises sequences encoding the last amino acid of the exlA pre-pro-sequence fused to the first 12 codons of the mature lipase encoding sequence. It contains a XhoI site for cloning and a NruI site, which comprises the last 3 base pairs of the exlA prosequence. The fragment ends with a BglII site. Vector pTL1-AflII was linearized by partial digestion with XhoI, followed by cutting with BglII, which cuts just within the region coding for the mature lipase. The 6.3 kb XhoI-BglII vector fragment (resulting from a cut at the XhoI site in the glaA promoter while leaving the internal XhoI site in the lipase gene intact, see FIG. 8) was isolated from an agarose gel and ligated with the synthetic XhoI-BglII fragment, resulting in pTL1-XB. From pTL1-XB an 0.83 kb NruI-AflII fragment was isolated containing the last 3 base pairs of the exlA prosequence followed by the sequence encoding the mature lipase polypeptide up to the AflII site just beyond the stop codon (see example 2). This fragment was ligated with the 7.2 kb NruI-AflII fragment of pAW14A-Not to give expression vector pAWTL2 (FIG. 7).

3.2 Production and secretion of Thermomyces lanuginosa using the exlA promoter and terminator.

The constructed expression vectors (pAWTL1 and pAWTL2) can subsequently be transferred to moulds (for example Aspergillus niger, Aspergillus niger var. awamori, Aspergillus nidulans etc.) by means of conventional co-transformation techniques and the lipase can then be expressed via induction of the endoxylanase II promoter. The constructed vector can also be provided with conventional selection markers (e.g. amdS or pyrG, hygromycin etc.) and the mould can be transformed with the resulting vector to produce the desired protein, essentially as described in example 2. As an example, plasmids were derived from pAWTL1 and pAWTL2 by introduction of an Aspergillus niger var. awamori pyrG gene, and the resulting plasmids were introduced in strain AWPYR, an Aspergillus niger var. awamori strain derived from strain CBS 115.52 (ATCC 11358) in which the pyrG gene has been disrupted. Following this route, transformant AWLPL1-2 was derived using the pAWTL1 plasmid, whereas transformant AWLPL2-2 was derived starting from the pAWTL2 plasmid.

Transformant AWLPL1-2 (containing the Thermomyces lanuginosa mature lipase encoding region with the Thermomyces lanuginosa signal sequence under the control of Aspergillus niger var. awamori exlA promoter and terminator) and transformant AWLPL2-2 (containing the Thermomyces lanuginosa mature lipase encoding region with the endoxylanase signal sequence under the control the Aspergillus niger awamori exlA promoter and terminator) were grown in shake flasks on AW Medium as described in example 2. Incubation took place at 30° C., 200 rpm for 24 hours in a Mk X incubator shaker. After growth cells were collected by filtration (0.45 µm filter), washed twice with AW Medium without sucrose and yeast extract (salt solution), resuspended in 50 ml salt solution and transferred to 300 ml shake flasks containing 50 ml salt solution to which xylose has been added to a final concentration of 10 g/l (induction medium). The moment of resuspension is referred to as "t=0" (start of induction). Incubation took place under the same conditions as described above. Samples were taken 15, 22 and 39 hours after induction. Samples were filtered over miracloth to remove biomass and the filtrate was analyzed for lipase activity by a titrimetric assay using olive oil as a substrate.

For each sample between 100 and 200 µl of filtrate was added to a stirred mixture of 5.0 ml lipase substrate (Sigma, containing olive oil as a substrate for the lipase) and 25.0 ml of buffer (5 mM Tris-HCl pH 9.0, 40 mM NaCl, 20 mM $CaCl_2$). The assay was carried out at 30° C. and the release of fatty acids was measured by automated titration with 0.05M NaOH to pH 9.0 using a Mettler DL25 titrator. A curve of the amount of titrant against time was obtained. The amount of lipase activity contained in the sample was calculated from the maximum slope of this curve. One unit of enzymatic activity is defined as the amount of enzyme that releases 1 µmol of fatty acid from olive oil in one minute under the conditions specified above. Such determinations are known to those skilled in the art.

The results are presented in Table D. From these results it is obvious that functional lipase is produced and secreted after induction of the exlA promoter by xylose, and that the exlA signal sequence can direct the secretion of heterologous proteins in Aspergillus niger var. awamori.

TABLE D

| | Production and secretion of lipase | | | | |
|---|---|---|---|---|---|
| Strain | exp | t = 0 | t = 15 | t = 22 | t = 39 |
| AWLPL1-2 | A | 3.2 | 76 | 65 | 59 |
| AWLPL1-2 | B | 7 | 84 | 32 | 35 |
| AWLPL2-2 | A | 9 | 77 | 50 | 49 |
| AWLPL2-2 | B | 8 | 72 | 51 | 46 |
| AW | A | 7 | 9 | 8 | 8 |
| AW | B | 6 | 7 | 7 | 8 |

Transformants were grown on synthetic medium as indicated in the text for 24 hours and at t=0 were transferred to induction medium as indicated in the text. Lipase activity in the medium was determined by a titrimetric assay using olive oil as substrate and is expressed in arbitrary units of lipase activity. A and B represent duplo experiments.

TABLE E

| Nucleotide sequences of oligonucleotides used in constructions | | |
|---|---|---|
| BTFF05 | 5'-TCGAGTCGCGAGAGGTCTCGCAA-3' | SEQ ID NO: 5 |
| BTFF06 | 5'-GATCTTGCGAGACCTCTCGCGAC-3' | SEQ ID NO: 6 |
| BTFF09 | 5'-TCGAGCGTCATGAGGAGCT-3' | SEQ ID NO: 7 |
| BTFF10 | 5'-CCTCATGACGC-3' | SEQ ID NO: 8 |
| Eco-Not | 5'-AATTGCGGCCGC-3' | SEQ ID NO: 9 |
| Hind-Afl | 5'-AGCTCGCTTAAGCG-3' | SEQ ID NO: 10 |
| Nco-Afl | 5'-CATGCCTTAAGG-3' | SEQ ID NO: 11 |
| Xyl11 | 5'-GCATATGATTAAGCTGC-3' | SEQ ID NO: 12 |

Sequence listing numbers refer to the listings provided in the official format.

LITERATURE REFERENCES

Fuller, R. S., Sterne, R. E. and Thorner J. (1988) Enzymes required for yeast prohormone processing. Ann. Rev. Physiol. 50, 345–362 van Heijne, G. (1986) A new method for preceding signal sequence cleavage sites. Nucl. Acids Res. 16, 4683–4690.

Roberts. N., Oliver, R. P., Punt, P. J. and van den Hondel, C. A. M. J. J. (1989) Expression of the *Escherichia coli* β-glucuronidase gene in industrial and phytopathogenic filamentous fungi. Curr. Genet. 15, 177–180.

Sambrook, J., Fritsch, E. F. and Maniatis, T. (1989) Molecular Cloning: A laboratory manual (2nd ed). Cold Spring Harbor Laboratory Press, Cold Spring Harbor, N.Y.

Sanger, F., Nicklan, S. and Coulson, A. R. (1977) DNA sequencing with chain-terminating inhibitors. Proc. Natl. Acad. Sci. USA 74, 5463–5467.

Ward, M., Wilson, L. J., Kodama, K. H., Rey, M. W. and Berka, R. M. (GENENCOR) (May 1990) Improved Production of Chymosin in Aspergillus by expression as a glucoamylase-chymosin fusion. Bio/Technology 8, 435–440.

CA-A-2024448 (ALLELIX BIOPHARMACE) "Recombinant DNA expression construct—containing promoter for use in Aspergillus", published on 1 Mar. 1991

EP-A-0436858 (GREEN CROSS CORP.) "Promoter of glyceraldehyde-3-phosphate dehydrogenase gene—derived from *Aspergillus orizae*, used in new expression system in yellow-green or black koji mould", published on 17 Jul. 1991

EP-A-0439997 (CIBA GEIGI AG) "*A. niger* pyruvate kinase promoter—used to construct vectors for expression of structural genes in suitable hosts", published on 7 Aug. 1991

WO 91/19782 (UNILEVER) "Xylanase production", published on 26 Dec. 1991, thus within the priority year

---

We claim:

1. A process for production of a protein which comprises culturing cells of a mould transformed with an expression vector comprising a gene encoding said protein operatively linked to at least one regulating region selected from the group consisting of a) expression and secretion regulating regions of the endoxylanase II gene (exlA gene) of *Aspergillus niger* var. awamori present on plasmid pAW14B (FIG. 3), which is present in a transformed *E. coli* strain JM109 deposited at the Centraalbureau voor Schimmelcultures in Baarn, The Netherlands, under N° CBS 237.90 on 31 May 1990, and b) functional derivatives of a) having at least one activity selected from the group consisting of expression and secretion regulating activity, wherein said protein is not endoxylanase type II ex *Aspergillus niger* var. awamori;

and wherein the gene encoding said protein is in frame with any secretion regulating region present.

2. The process according to claim 1 wherein the selected expression regulating region is a promoter and said vector comprises a gene encoding said protein under control of said promoter, the latter being selected from the group consisting of a) the promoter of the endoxylanase II gene (exlA gene) of *Aspergillus niger* var. awamori present on plasmid pAW14B (FIG. 3), which is present in a transformed *E. coli* strain JM109 deposited at the Centraalbureau voor Schimmelcultures in Baarn, The Netherlands, under N° CBS 237.90 on 31 May 1990, and b) functional derivatives of a) also having promoter activity.

3. The process according to claim 2, in which said promoter corresponds with the promoter present on the 5' part upstream of the exlA gene having a size of about 2.5 kb located between the SalI restriction site at position 0 and the start codon ATG of the exlA gene in plasmid pAW14B.

4. The process according to claim 2, in which said promoter comprises at least the polynucleotide sequence 1-350 according to FIG. 1 (SEQ ID NO:1).

5. The process according to claim 2, in which said promoter is induced by wheat bran, xylan, or xylose, or a mixture of any combination thereof, present in a medium in which the transformed mould is incubated.

6. The process according to claim 5, in which said promoter is induced by xylose present in the medium in which the transformed mould is incubated.

7. The process according to claim 1 wherein the selected expression regulating region is a terminator and said vector comprises a gene encoding said protein followed by said terminator, the latter being selected from the group consisting of
- a) the terminator of the endoxylanase II gene (exlA gene) of *Aspergillus niger* var. awamori present on plasmid pAW14B (FIG. 3), which is present in a transformed *E. coli* strain JM109 deposited at the Centraalbureau voor Schimmelcultures in Baarn, The Netherlands, under N° CBS 237.90 on 31 May 1990, and
- b) functional derivatives of a) also having terminator activity.

8. The process according to claim 7, in which said terminator corresponds with the terminator present on the 3' part downstream of the exlA gene having a size of about 1.0 kb located right downstream of the stop codon (TAA) of the exlA gene in plasmid pAW14B.

9. The process according to claim 7, in which said vector also comprises a promoter and said vector comprises a gene encoding said protein under control of said promoter, the latter being selected from the group consisting of
- a) the promoter of the endoxylanase II gene (exlA gene) of *Aspergillus niger* var. awamori present on plasmid pAW14B (FIG. 3), which is present in a transformed *E. coli* strain JM109 deposited at the Centraalbureau voor Schimmelcultures in Baarn, The Netherlands, under N° CBS 237.90 on 31 May 1990, and
- b) functional derivatives of a) also having promoter activity.

10. A process according to claim 1 for the production and secretion of a protein by means of a transformed mould, wherein the selected secretion regulating region is a DNA sequence encoding a signal sequence and said vector comprises a gene encoding said protein preceded by said DNA sequence encoding a signal sequence, the latter being selected from the group consisting of
- a) the DNA sequence encoding the signal sequence of the endoxylanase II gene (exlA gene) of *Aspergillus niger* var. awamori present on plasmid pAW14B (FIG. 3), which is present in a transformed *E. coli* strain JM109 deposited at the Centraalbureau voor Schimmelcultures in Baarn, The Netherlands, under N° CBS 237.90 on 31 May 1990, and
- b) functional derivatives of a) also directing secretion of the protein;

and wherein the gene encoding said protein is in frame with said DNA encoding the signal sequence.

11. The process according to claim 10, in which the gene encoding said protein is also preceded by at least an essential part of a DNA sequence encoding the mature endoxylanase II protein, whereby said essential part of said DNA sequence is present between said DNA sequence encoding a signal sequence and the gene, and wherein the gene encoding said protein is in frame with both said DNA encoding a signal sequence and the essential part of said DNA sequence encoding the mature endoxylanase II protein.

12. The process according to claim 10, in which said signal sequence is the signal sequence encoded by polynucleotide 351–431 of the DNA sequence given in FIG. 1 (SEQ ID NO:1), which polynucleotide precedes the exlA gene in plasmid pAW14B.

13. The process according to claim 10, in which said vector also comprises at least one of
- a) a promoter and said vector comprises a gene encoding said protein under control of said promoter, the latter being selected from the group consisting of the promoter of the endoxylanase II gene (exlA gene) of *Aspergillus niger* var. awamori present on plasmid pAW14B (FIG. 3), which is present in a transformed *E. coli* strain JM109 deposited at the Centraalbureau voor Schimmelcultures in Baarn, The Netherlands, under N° CBS 237.90 on 31 May 1990, and functional derivatives thereof also having promoter activity and
- b) a terminator and said vector comprises a gene encoding said protein followed by said terminator, the latter being selected from the terminator of the endoxylanase II gene (exlA gene) of *Aspergillus niger* var. awamori present on plasmid pAW14B (FIG. 3), which is present in a transformed *E. coli* strain JM109 deposited at the Centraalbureau voor Schimmelcultures in Baarn, The Netherlands, under N° CBS 237.90 on 31 May 1990, and functional derivatives thereof also having terminator activity.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 2059 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Aspergillus niger var. awamori
        ( B ) STRAIN: CBS 115.52 (ATCC 11358)

( v i i ) IMMEDIATE SOURCE:
        ( B ) CLONE: pAW14B ( i x ) FEATURE:
        ( A ) NAME/KEY: intron
        ( B ) LOCATION: 581..629
        ( C ) IDENTIFICATION METHOD: experimental
        ( D ) OTHER INFORMATION: /evidence=EXPERIMENTAL ( i x ) FEATURE:
        ( A ) NAME/KEY: promoter
        ( B ) LOCATION: 1..350
        ( C ) IDENTIFICATION METHOD: experimental
        ( D ) OTHER INFORMATION: /evidence=EXPERIMENTAL ( i x ) FEATURE:
        ( A ) NAME/KEY: sig_peptide
        ( B ) LOCATION: 351..431

( i x ) FEATURE:
    ( A ) NAME/KEY: mat_peptide
    ( B ) LOCATION: join(432..580, 630..1032)
    ( C ) IDENTIFICATION METHOD: experimental
    ( D ) OTHER INFORMATION: /EC_number=3.2.1.8
        / product="endoxylanase II"
        / evidence=EXPERIMENTAL
        / gene="exlA"

( i x ) FEATURE:
    ( A ) NAME/KEY: CDS
    ( B ) LOCATION: join(351..580, 630..1035)
    ( C ) IDENTIFICATION METHOD: experimental
    ( D ) OTHER INFORMATION: /EC_number=3.2.1.8
        / product="pre-pro endoxylanase II"
        / evidence=EXPERIMENTAL
        / gene="exlA"

( x i ) SEQUENCE DESCRIPTION: SEQ ID NO:1:

```
AGCCCTTTTA  TCCGTCTGCC  GTCCATTTAG  CCAAATGTAG  TCCATTTAGC  CAAGTGCGGT      60

CCATTTAGCC  AAGACCAGTG  GCTAGATTGG  TGGCTACACA  GCAAACGCAT  GACTGAGACA     120

CAACTATAGG  ACTGTCTCTG  GAAATAGGCT  CGAGGTTGTT  CAAGCGTTTA  AGGTGATGCG     180

GCAAAATGCA  TATGACTAAG  CTGCTTCATC  TTGCAGGGGG  AAGGGATAAA  TAGTCTTTTT     240

CGCAGAATAT  AAATAGAGGT  AGAGTGGGCT  CGCAGCAATA  TTGACCAGCA  CAGTGCTTCT     300

CTTCCAGTTG  CATAAATCCA  TTCACCAGCA  TTTAGCTTTC  TTCAATCATC  ATG AAG        356
                                                           Met Lys
                                                           -27

GTC ACT GCG GCT TTT GCA GGT CTT TTG GTC ACG GCA TTC GCC GCT CCT            404
Val Thr Ala Ala Phe Ala Gly Leu Leu Val Thr Ala Phe Ala Ala Pro
-25              -20              -15              -10

GTG CCG GAA CCT GTT CTG GTG TCG CGA AGT GCT GGT ATT AAC TAC GTG            452
Val Pro Glu Pro Val Leu Val Ser Arg Ser Ala Gly Ile Asn Tyr Val
             -5               1               5

CAA AAC TAC AAC GGC AAC CTT GGT GAT TTC ACC TAT GAC GAG AGT GCC            500
Gln Asn Tyr Asn Gly Asn Leu Gly Asp Phe Thr Tyr Asp Glu Ser Ala
        10              15              20

GGA ACA TTT TCC ATG TAC TGG GAA GAT GGA GTG AGC TCC GAC TTT GTC            548
Gly Thr Phe Ser Met Tyr Trp Glu Asp Gly Val Ser Ser Asp Phe Val
    25              30              35

GTT GGT CTG GGC TGG ACC ACT GGT TCT TCT  AA GTGAGTGACT                     590
Val Gly Leu Gly Trp Thr Thr Gly Ser Ser Asn
    40              45              50

GTATTCTTTA  ACCAAAGTCT  AGGATCTAAC  GTTTTCTAG C GCT ATC ACC TAC TCT        645
                                              Ala Ile Thr Tyr Ser
                                                              55

GCC GAA TAC AGT GCT TCT GGC TCC TCT TCC TAC CTC GCT GTG TAC GGC            693
Ala Glu Tyr Ser Ala Ser Gly Ser Ser Ser Tyr Leu Ala Val Tyr Gly
            60              65              70

TGG GTC AAC TAT CCT CAG GCT GAA TAC TAC ATC GTC GAG GAT TAC GGT            741
Trp Val Asn Tyr Pro Gln Ala Glu Tyr Tyr Ile Val Glu Asp Tyr Gly
        75              80              85

GAT TAC AAC CCT TGC AGC TCG GCC ACA AGC CTT GGT ACC GTG TAC TCT            789
Asp Tyr Asn Pro Cys Ser Ser Ala Thr Ser Leu Gly Thr Val Tyr Ser
    90              95              100

GAT GGA AGC ACC TAC CAA GTC TGC ACC GAC ACT CGA ACT AAC GAA CCG            837
Asp Gly Ser Thr Tyr Gln Val Cys Thr Asp Thr Arg Thr Asn Glu Pro
105             110             115

TCC ATC ACG GGA ACA AGC ACG TTC ACG CAG TAC TTC TCC GTT CGA GAG            885
Ser Ile Thr Gly Thr Ser Thr Phe Thr Gln Tyr Phe Ser Val Arg Glu
120             125             130             135

AGC ACG CGC ACA TCT GGA ACG GTG ACT GTT GCC AAC CAT TTC AAC TTC            933
Ser Thr Arg Thr Ser Gly Thr Val Thr Val Ala Asn His Phe Asn Phe
```

-continued

```
                         140                      145                       150
TGG GCG CAG CAT GGG TTC GGA AAT AGC GAC TTC AAT TAT CAG GTC ATG                  981
Trp Ala Gln His Gly Phe Gly Asn Ser Asp Phe Asn Tyr Gln Val Met
             155                 160                     165

GCA GTG GAA GCA TGG AGC GGT GCT GGC AGC GCC AGT GTC ACG ATC TCC                 1029
Ala Val Glu Ala Trp Ser Gly Ala Gly Ser Ala Ser Val Thr Ile Ser
         170                 175                     180

TCT TAAGGGATAA GTGCCTTGGT AGTCGGAAGA TGTCAACGCG GAACTTTGTT                      1082
Ser
    185

CTCAGCTGGT GTGATGATCG GATCCGGCCT CTGGTGGTTA CATTGAGGCT GTATAAGTTA              1142
TTCTGGGGCC GAGCTGTCAG CGGCTGCGTT TCCAATTTGC ACAGATAATC AACTTTCGTT              1202
TTCTATCTCT TGCGTTTCCA CGCTGTTTAT CCTATCCATA GATAATATTT TGCCCAATAC              1262
ATATTATCTA TATACAACTT GTTCGGTCGC AGTAGTCACT CCGAGCAAGG CATTGGGAAA              1322
TTGGGAGATG CGGGGTGCTG CGTACGCTCT AAGGTAGGGC ATTTAAGGG ATATTTAGCC               1382
TCCAGATATT CTATACTAAC AGACTTCTAA TGACTGCGGA TAATATAGAG GGCAAGAATT              1442
TCTACAGTTC GACGCAGTTC AACGCAATCA GAGAGGGAAT ACTGATGAGA GTGCAATCAG              1502
TTAGAGAAGG ACAACATGGC AGTCTTAGTG TGAACTTACA TAACGATATG GACTCTAGAA              1562
AAAAGGAAGG AGCTCCGTCT ATATATAGCG CCATTACGTG TATCTGATGC TTGCCCATTG              1622
CCACTGGGTA GGGTGACTTT TTGAAGCGAC TCGACATATA ATATGACAAA CTCATGCCCC              1682
CTTTGCAGGA AACTTAGCTT TTCCTGCCTT GCTTGAAGC CACAATTATC ACGAAACTCA               1742
TTTAGAGATT TATCTTCCTG TAACGGAAAC AAATATTTCG GGATTGGAAT AGCCTTTTGC              1802
CGAACTCATT ATTTTTTGC GACGGTAAAT CTGGGAGTAT ACGATGTCCT TTCACGTTTC               1862
TCAACAAAAC TCTGCCGCAC CGGGTAACCT ACGGATAGTA CTGTATCCAG ACTCAGTTTT              1922
TCTAATAACA GGACACTGTG CAATTGCGG GAAAATTCCT ATGTATATTA CTTTCTCGTT               1982
GCATCTCAAA TATTGTGGCT TTTTGAGACC CACACTATGT CTTGCACATA TTGTACCATC              2042
CTTGCTTGAG GCCAATT                                                             2059
```

(2) INFORMATION FOR SEQ ID NO:2:

(i) SEQUENCE CHARACTERISTICS:
        (A) LENGTH: 211 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Val Thr Ala Ala Phe Ala Gly Leu Leu Val Thr Ala Phe Ala
-27         -25                 -20                 -15

Ala Pro Val Pro Glu Pro Val Leu Val Ser Arg Ser Ala Gly Ile Asn
    -10                  -5                   1                 5

Tyr Val Gln Asn Tyr Asn Gly Asn Leu Gly Asp Phe Thr Tyr Asp Glu
                     10                  15                 20

Ser Ala Gly Thr Phe Ser Met Tyr Trp Glu Asp Gly Val Ser Ser Asp
             25                  30                 35

Phe Val Val Gly Leu Gly Trp Thr Thr Gly Ser Ser Asn Ala Ile Thr
             40                  45                 50

Tyr Ser Ala Glu Tyr Ser Ala Ser Gly Ser Ser Ser Tyr Leu Ala Val
         55                  60                  65

Tyr Gly Trp Val Asn Tyr Pro Gln Ala Glu Tyr Tyr Ile Val Glu Asp
 70                  75                  80                 85
```

```
Tyr Gly Asp Tyr Asn Pro Cys Ser Ser Ala Thr Ser Leu Gly Thr Val
                 90                  95                    100

Tyr Ser Asp Gly Ser Thr Tyr Gln Val Cys Thr Asp Thr Arg Thr Asn
            105              110             115

Glu Pro Ser Ile Thr Gly Thr Ser Thr Phe Thr Gln Tyr Phe Ser Val
        120              125              130

Arg Glu Ser Thr Arg Thr Ser Gly Thr Val Thr Val Ala Asn His Phe
    135              140              145

Asn Phe Trp Ala Gln His Gly Phe Gly Asn Ser Asp Phe Asn Tyr Gln
150             155                  160              165

Val Met Ala Val Glu Ala Trp Ser Gly Ala Gly Ser Ala Ser Val Thr
            170              175              180

Ile Ser Ser
```

(2) INFORMATION FOR SEQ ID NO:3:

(i) SEQUENCE CHARACTERISTICS:
        (A) LENGTH: 886 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..876
        (C) IDENTIFICATION METHOD: experimental
        (D) OTHER INFORMATION: /product="Thermomyces lanuginosa
            pre-pro lipase"
        / evidence=EXPERIMENTAL (ix) FEATURE:
        (A) NAME/KEY: mat_peptide
        (B) LOCATION: 67..873
        (C) IDENTIFICATION METHOD: experimental
        (D) OTHER INFORMATION: /product="Thermomyces lanuginosa
            lipase"
        / evidence=EXPERIMENTAL (xi) SEQUENCE DESCRIPTION: SEQ ID NO:3:

```
ATG AGG AGC TCC CTT GTG CTG TTC TTT GTC TCT GCG TGG ACG GCC TTG        48
Met Arg Ser Ser Leu Val Leu Phe Phe Val Ser Ala Trp Thr Ala Leu
-22     -20                 -15                 -10

GCC AGT CCT ATT CGT CGA GAG GTC TCG CAA GAT CTG TTT AAC CAG TTC        96
Ala Ser Pro Ile Arg Arg Glu Val Ser Gln Asp Leu Phe Asn Gln Phe
    -5               1               5                    10

AAT CTC TTT GCA CAG TAT TCT GCT GCC GCA TAC TGC GGA AAA AAC AAT       144
Asn Leu Phe Ala Gln Tyr Ser Ala Ala Ala Tyr Cys Gly Lys Asn Asn
                15                  20                  25

GAT GCC CCA GCT GGT ACA AAC ATT ACG TGC ACG GGA AAT GCC TGC CCC       192
Asp Ala Pro Ala Gly Thr Asn Ile Thr Cys Thr Gly Asn Ala Cys Pro
            30                  35                  40

GAG GTA GAG AAG GCG GAT GCA ACG TTT CTC TAC TCG TTT GAA GAC TCT       240
Glu Val Glu Lys Ala Asp Ala Thr Phe Leu Tyr Ser Phe Glu Asp Ser
        45                  50                  55

GGA GTG GGC GAT GTC ACC GGC TTC CTT GCT CTA GAC AAC ACG AAC AAA       288
Gly Val Gly Asp Val Thr Gly Phe Leu Ala Leu Asp Asn Thr Asn Lys
        60                  65                  70

TTG ATC GTC CTC TCT TTC CGT GGC TCT CGT TCC ATA GAA AAC TGG ATC       336
Leu Ile Val Leu Ser Phe Arg Gly Ser Arg Ser Ile Glu Asn Trp Ile
75                  80                  85                  90

GGA AAT CTT AAC TTC GAC TTG AAA GAA ATA AAT GAC ATT TGC TCC GGC   384
    Gly Asn Leu Asn Phe Asp Leu Lys Glu Ile Asn Asp Ile Cys Ser Gly
                    95                  100                 105
```

```
TGC  AGG  GGA  CAT  GAC  GGC  TTC  ACC  TCG  AGC  TGG  AGG  TCT  GTA  GCC  GAT       432
Cys  Arg  Gly  His  Asp  Gly  Phe  Thr  Ser  Ser  Trp  Arg  Ser  Val  Ala  Asp
          110                      115                      120

ACG  TTA  AGG  CAG  AAG  GTG  GAG  GAT  GCT  GTG  AGG  GAG  CAT  CCC  GAC  TAT       480
Thr  Leu  Arg  Gln  Lys  Val  Glu  Asp  Ala  Val  Arg  Glu  His  Pro  Asp  Tyr
          125                      130                      135

CGC  GTG  GTG  TTT  ACC  GGA  CAT  AGC  TTG  GGT  GGT  GCA  TTG  GCA  ACT  GTT       528
Arg  Val  Val  Phe  Thr  Gly  His  Ser  Leu  Gly  Gly  Ala  Leu  Ala  Thr  Val
     140                      145                      150

GCC  GGA  GCA  GAC  CTG  CGT  GGA  AAT  GGG  TAT  GAC  ATC  GAC  GTG  TTT  TCA       576
Ala  Gly  Ala  Asp  Leu  Arg  Gly  Asn  Gly  Tyr  Asp  Ile  Asp  Val  Phe  Ser
155                      160                      165                      170

TAT  GGC  GCC  CCC  CGA  GTC  GGA  AAC  AGG  GCT  TTT  GCA  GAA  TTC  CTG  ACC       624
Tyr  Gly  Ala  Pro  Arg  Val  Gly  Asn  Arg  Ala  Phe  Ala  Glu  Phe  Leu  Thr
               175                      180                      185

GTA  CAG  ACC  GGC  GGT  ACC  CTC  TAC  CGC  ATT  ACC  CAC  ACC  AAT  GAT  ATT       672
Val  Gln  Thr  Gly  Gly  Thr  Leu  Tyr  Arg  Ile  Thr  His  Thr  Asn  Asp  Ile
               190                      195                      200

GTC  CCT  AGA  CTC  CCG  CCG  CGC  GAG  TTC  GGT  TAC  AGC  CAT  TCT  AGC  CCA       720
Val  Pro  Arg  Leu  Pro  Pro  Arg  Glu  Phe  Gly  Tyr  Ser  His  Ser  Ser  Pro
          205                      210                      215

GAG  TAC  TGG  ATC  AAA  TCT  GGA  ACC  CTT  GTC  CCC  GTC  ACC  CGA  AAC  GAC       768
Glu  Tyr  Trp  Ile  Lys  Ser  Gly  Thr  Leu  Val  Pro  Val  Thr  Arg  Asn  Asp
     220                      225                      230

ATC  GTG  AAG  ATA  GAA  GGC  ATC  GAT  GCC  ACC  GGC  GGC  AAT  AAC  CAG  CCT       816
Ile  Val  Lys  Ile  Glu  Gly  Ile  Asp  Ala  Thr  Gly  Gly  Asn  Asn  Gln  Pro
235                      240                      245                      250

AAC  ATT  CCG  GAT  ATC  CCT  GCG  CAC  CTA  TGG  TAC  TTC  GGG  TTA  ATT  GGG       864
Asn  Ile  Pro  Asp  Ile  Pro  Ala  His  Leu  Trp  Tyr  Phe  Gly  Leu  Ile  Gly
               255                      260                      265

ACA  TGT  CTT  TAGTGCGAAG  CTT                                                       886
Thr  Cys  Leu
          270
```

( 2 ) INFORMATION FOR SEQ ID NO:4:

( i ) SEQUENCE CHARACTERISTICS:
        ( A ) LENGTH: 291 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Arg  Ser  Ser  Leu  Val  Leu  Phe  Phe  Val  Ser  Ala  Trp  Thr  Ala  Leu
-22       -20                      -15                      -10

Ala  Ser  Pro  Ile  Arg  Arg  Glu  Val  Ser  Gln  Asp  Leu  Phe  Asn  Gln  Phe
          -5                   1                   5                       10

Asn  Leu  Phe  Ala  Gln  Tyr  Ser  Ala  Ala  Tyr  Cys  Gly  Lys  Asn  Asn
                    15                      20                      25

Asp  Ala  Pro  Ala  Gly  Thr  Asn  Ile  Thr  Cys  Thr  Gly  Asn  Ala  Cys  Pro
                    30                      35                      40

Glu  Val  Glu  Lys  Ala  Asp  Ala  Thr  Phe  Leu  Tyr  Ser  Phe  Glu  Asp  Ser
               45                      50                      55

Gly  Val  Gly  Asp  Val  Thr  Gly  Phe  Leu  Ala  Leu  Asp  Asn  Thr  Asn  Lys
          60                      65                      70

Leu  Ile  Val  Leu  Ser  Phe  Arg  Gly  Ser  Arg  Ser  Ile  Glu  Asn  Trp  Ile
75                      80                      85                      90

Gly  Asn  Leu  Asn  Phe  Asp  Leu  Lys  Glu  Ile  Asn  Asp  Ile  Cys  Ser  Gly
                    95                      100                     105
```

| | | | | | | | | | | | | | | |
|---|---|---|---|---|---|---|---|---|---|---|---|---|---|---|
|Cys|Arg|Gly|His 110|Asp|Gly|Phe|Thr|Ser 115|Ser|Trp|Arg|Ser|Val 120|Ala|Asp|
|Thr|Leu|Arg 125|Gln|Lys|Val|Glu|Asp 130|Ala|Val|Arg|Glu|His 135|Pro|Asp|Tyr|
|Arg|Val 140|Val|Phe|Thr|Gly|His 145|Ser|Leu|Gly|Gly|Ala 150|Leu|Ala|Thr|Val|
|Ala 155|Gly|Ala|Asp|Leu|Arg 160|Gly|Asn|Gly|Tyr|Asp 165|Ile|Asp|Val|Phe|Ser 170|
|Tyr|Gly|Ala|Pro|Arg 175|Val|Gly|Asn|Arg|Ala 180|Phe|Ala|Glu|Phe|Leu 185|Thr|
|Val|Gln|Thr|Gly 190|Gly|Thr|Leu|Tyr|Arg 195|Ile|Thr|His|Thr|Asn 200|Asp|Ile|
|Val|Pro|Arg 205|Leu|Pro|Pro|Arg|Glu 210|Phe|Gly|Tyr|Ser|His 215|Ser|Ser|Pro|
|Glu|Tyr 220|Trp|Ile|Lys|Ser|Gly 225|Thr|Leu|Val|Pro|Val 230|Thr|Arg|Asn|Asp|
|Ile 235|Val|Lys|Ile|Glu|Gly 240|Ile|Asp|Ala|Thr|Gly 245|Gly|Asn|Asn|Gln|Pro 250|
|Asn|Ile|Pro|Asp|Ile 255|Pro|Ala|His|Leu|Trp 260|Tyr|Phe|Gly|Leu|Ile 265|Gly|
|Thr|Cys|Leu| | | | | | | | | | | | | |

(2) INFORMATION FOR SEQ ID NO:5:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:5:

TCGAGTCGCG AGAGGTCTCG CAA      23

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:6:

GATCTTGCGA GACCTCTCGC GAC      23

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:7:

TCGAGCGTCA TGAGGAGCT      19

(2) INFORMATION FOR SEQ ID NO:8:

(i) SEQUENCE CHARACTERISTICS:
        (A) LENGTH: 11 base pairs
        (B) TYPE: nucleic acid
        (C) STRANDEDNESS: single
        (D) TOPOLOGY: linear ( x i ) SEQUENCE DESCRIPTION: SEQ ID NO:8:

CCTCATGACG C                                                                                                                              1 1

( 2 ) INFORMATION FOR SEQ ID NO:9:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

AATTGCGGCC GC                                                                                                                             1 2

( 2 ) INFORMATION FOR SEQ ID NO:10:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

AGCTCGCTTA AGCG                                                                                                                           1 4

( 2 ) INFORMATION FOR SEQ ID NO:11:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

CATGCCTTAA GG                                                                                                                             1 2

( 2 ) INFORMATION FOR SEQ ID NO:12:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

GCATATGATT AAGCTGC                                                                                                                        1 7